(12) United States Patent
Johnson

(10) Patent No.: US 9,125,911 B2
(45) Date of Patent: Sep. 8, 2015

(54) COMBINED SYSTEMIC AND TOPICAL TREATMENT OF DISORDERED TISSUES

(71) Applicant: QUADEX PHARMACEUTICALS, LLC, Midvale, UT (US)

(72) Inventor: B. Ron Johnson, Sandy, UT (US)

(73) Assignee: QUADEX PHARMACEUTICALS, LLC, Midvale, UT (US)

( * ) Notice: Subject to any disclaimer, the term of this patent is extended or adjusted under 35 U.S.C. 154(b) by 39 days.

(21) Appl. No.: 13/804,002

(22) Filed: Mar. 14, 2013

(65) Prior Publication Data

US 2014/0274939 A1 Sep. 18, 2014

(51) Int. Cl.
| | | |
|---|---|---|
| *A01N 43/04* | (2006.01) | |
| *A61K 31/70* | (2006.01) | |
| *A61K 31/522* | (2006.01) | |
| *A61K 31/14* | (2006.01) | |
| *A61K 31/7072* | (2006.01) | |
| *A61K 31/52* | (2006.01) | |
| *A61K 31/662* | (2006.01) | |
| *A61K 31/675* | (2006.01) | |
| *A61K 31/7125* | (2006.01) | |

(52) U.S. Cl.
CPC .............. *A61K 31/522* (2013.01); *A61K 31/14* (2013.01); *A61K 31/52* (2013.01); *A61K 31/662* (2013.01); *A61K 31/675* (2013.01); *A61K 31/7072* (2013.01); *A61K 31/7125* (2013.01)

(58) Field of Classification Search
None
See application file for complete search history.

(56) References Cited

U.S. PATENT DOCUMENTS

| | | |
|---|---|---|
| 1,519,693 A | 12/1924 | Moore |
| 1,822,566 A | 9/1931 | Davies |
| 3,369,543 A | 2/1968 | Ronco |
| 3,614,245 A | 10/1971 | Schwartzman |
| 3,620,807 A | 11/1971 | Murray |
| 4,176,197 A | 11/1979 | Olson |
| 4,183,684 A | 1/1980 | Avery, Jr. |
| 4,199,574 A | 4/1980 | Schaeffer |
| 4,262,007 A | 4/1981 | Sherrill |
| 4,390,539 A | 6/1983 | Sherrill |
| 4,394,381 A | 7/1983 | Sherrill |
| 4,420,484 A | 12/1983 | Gorman et al. |
| 4,464,398 A | 8/1984 | Sheets et al. |
| 4,486,450 A | 12/1984 | Bernstein |
| 4,507,281 A | 3/1985 | Asculai et al. |
| 4,523,589 A | 6/1985 | Krauser |
| 4,532,128 A | 7/1985 | Sheldon et al. |
| 4,556,557 A | 12/1985 | Reichert |
| 4,599,335 A | 7/1986 | Rentzea et al. |
| 4,661,354 A | 4/1987 | Finnerty |
| 4,745,132 A | 5/1988 | Swered et al. |
| 4,778,813 A | 10/1988 | Fenyes et al. |
| 4,797,420 A | 1/1989 | Bryant |
| 4,820,737 A | 4/1989 | Schoenwald et al. |
| 4,822,605 A | 4/1989 | Powell |
| 4,828,542 A | 5/1989 | Hermann |
| 4,870,108 A | 9/1989 | Page |
| 4,874,794 A | 10/1989 | Katz |
| 4,875,602 A | 10/1989 | Chickering et al. |
| 4,887,994 A | 12/1989 | Bedford |
| 4,895,727 A | 1/1990 | Allen |
| 4,898,888 A | 2/1990 | Baldone |
| 4,902,720 A | 2/1990 | Baldone |
| 4,914,132 A | 4/1990 | Donofrio et al. |
| 4,923,899 A | 5/1990 | Wachman et al. |
| 4,929,442 A | 5/1990 | Powell |
| 4,952,204 A | 8/1990 | Korteweg |
| 4,957,734 A | 9/1990 | Miller |
| 4,975,217 A | 12/1990 | Brown-Skyrobot et al. |
| 4,983,635 A | 1/1991 | Martin |
| 4,994,199 A | 2/1991 | Scardera et al. |
| 5,008,098 A | 4/1991 | Bernadiner et al. |
| 5,016,651 A | 5/1991 | Stalcup et al. |
| 5,026,561 A | 6/1991 | Bourbon et al. |
| 5,030,659 A | 7/1991 | Bansemir et al. |
| 5,036,095 A | 7/1991 | Andermann |
| 5,039,688 A | 8/1991 | Lewis |

(Continued)

FOREIGN PATENT DOCUMENTS

| | | |
|---|---|---|
| CA | 2143136 | 8/1996 |
| CA | 2259709 | 6/1999 |

(Continued)

OTHER PUBLICATIONS

Neyts et al. Antiviral Research (1998), vol. 40, pp. 53-56.*

(Continued)

*Primary Examiner* — Patrick Lewis
(74) *Attorney, Agent, or Firm* — Workman Nydegger

(57) ABSTRACT

Kits and methods for treating disordered tissue caused by a virus in a mammal involve co-administration of a systemic anti-virus drug and topically administering an anti-infective composition. The systemic anti-virus drug is internally administered and disrupts or inhibits virus replication systemically within the mammal. Examples include nucleoside analogues, nucleoside analogue precursors, and nucleotide analogues. The topically administered anti-infective composition includes at least one anti-infective agent, such as an organohalide (e.g., benzalkonium chloride), and is formulated to penetrate below the disordered tissue surface and allow the anti-infective agent to kill viruses at the disordered tissue site. The anti-infective composition reduces the time and/or number of dosages required for the systemic anti-virus drug to treat the disordered tissue in the absence of topically administering the anti-infective composition. It also reduces or eliminates incidences of post-treatment neuralgia.

23 Claims, 1 Drawing Sheet

(56) References Cited

U.S. PATENT DOCUMENTS

| | | |
|---|---|---|
| 5,124,359 A | 6/1992 | Wachman et al. |
| 5,137,724 A | 8/1992 | Balzarini et al. |
| 5,158,766 A | 10/1992 | Greenwald et al. |
| 5,198,217 A | 3/1993 | Vedros |
| 5,284,875 A | 2/1994 | Martin |
| 5,320,805 A | 6/1994 | Kramer et al. |
| 5,338,748 A | 8/1994 | Wachman et al. |
| 5,344,838 A | 9/1994 | Wachman et al. |
| 5,387,611 A | 2/1995 | Rubinstein |
| 5,403,864 A | 4/1995 | Bruch et al. |
| 5,405,602 A | 4/1995 | Simmons et al. |
| 5,439,685 A | 8/1995 | Augros |
| 5,446,014 A | 8/1995 | Schuppiser et al. |
| 5,492,932 A | 2/1996 | Kundsin |
| 5,503,853 A | 4/1996 | Bollen et al. |
| 5,514,640 A | 5/1996 | Jones et al. |
| 5,516,758 A | 5/1996 | Stevens et al. |
| 5,527,534 A | 6/1996 | Myhling |
| 5,531,984 A | 7/1996 | Staats |
| 5,540,934 A | 7/1996 | Touitou |
| 5,580,571 A | 12/1996 | Hostetler |
| 5,631,245 A | 5/1997 | Drube |
| 5,637,307 A | 6/1997 | Simmons et al. |
| 5,661,170 A | 8/1997 | Chodosh |
| 5,678,273 A | 10/1997 | Porcelli |
| 5,704,906 A | 1/1998 | Fox |
| 5,709,866 A | 1/1998 | Booras et al. |
| 5,712,257 A | 1/1998 | Carter |
| 5,725,875 A | 3/1998 | Noll et al. |
| 5,753,270 A | 5/1998 | Beauchamp et al. |
| 5,753,711 A | 5/1998 | Schwabe et al. |
| 5,762,940 A | 6/1998 | Bourbon et al. |
| 5,767,163 A | 6/1998 | Kundsin |
| 5,827,870 A | 10/1998 | Chodosh |
| 5,897,872 A | 4/1999 | Picciano |
| 5,906,814 A | 5/1999 | Epstein |
| 5,922,693 A | 7/1999 | Oldenhove |
| 5,939,461 A | 8/1999 | Siqueira |
| 5,962,391 A | 10/1999 | Oldenhove |
| 5,968,986 A | 10/1999 | Dyer |
| 5,994,383 A | 11/1999 | Dyer et al. |
| 5,997,893 A | 12/1999 | Jampani et al. |
| 6,013,677 A | 1/2000 | Dyer |
| 6,068,851 A | 5/2000 | Bergeron et al. |
| 6,087,400 A | 7/2000 | Dyer et al. |
| 6,165,494 A | 12/2000 | Picciano |
| 6,171,611 B1 | 1/2001 | Picciano |
| 6,187,332 B1 | 2/2001 | Gern et al. |
| 6,211,243 B1 | 4/2001 | Johnson |
| 6,248,343 B1 | 6/2001 | Jampani et al. |
| 6,284,289 B1 | 9/2001 | Van den Berghe |
| 6,329,353 B1 | 12/2001 | Dalrymple et al. |
| 6,342,537 B1 | 1/2002 | Thomsen et al. |
| 6,344,210 B2 | 2/2002 | Fust |
| 6,348,503 B1 | 2/2002 | Squires |
| 6,350,784 B1 | 2/2002 | Squires |
| 6,355,684 B1 | 3/2002 | Squires |
| 6,410,599 B1 | 6/2002 | Johnson |
| 6,414,032 B1 | 7/2002 | Johnson |
| 6,419,850 B1 | 7/2002 | Rouleau |
| 6,420,431 B1 | 7/2002 | Johnson |
| 6,423,750 B1 | 7/2002 | Johnson |
| 6,436,885 B2 | 8/2002 | Biedermann et al. |
| 6,441,045 B1 | 8/2002 | Birnbaum |
| 6,444,707 B1 | 9/2002 | Lampe et al. |
| 6,525,034 B2 | 2/2003 | Dalrymple et al. |
| 6,635,676 B2 | 10/2003 | Baker et al. |
| 6,759,434 B2 | 7/2004 | Johnson |
| 8,173,709 B2 | 5/2012 | Johnson |
| 8,217,080 B2 | 7/2012 | Johnson |
| 8,388,991 B2 | 3/2013 | Sondgeroth et al. |
| 8,470,346 B2 | 6/2013 | Chen |
| 8,598,106 B2 | 12/2013 | Schwarz et al. |
| 2001/0007651 A1 | 7/2001 | Fust |
| 2002/0006961 A1 | 1/2002 | Katz et al. |
| 2002/0136768 A1 | 9/2002 | Staats |
| 2002/0151521 A1 | 10/2002 | Burke et al. |
| 2002/0161046 A1 | 10/2002 | Konowalchuk et al. |
| 2002/0165277 A1 | 11/2002 | Konowalchuk et al. |
| 2002/0165278 A1 | 11/2002 | Konowalchuk et al. |
| 2002/0188028 A1 | 12/2002 | Johnson |
| 2002/0197212 A1 | 12/2002 | Osbakken et al. |
| 2003/0013769 A1 | 1/2003 | Mukkamala et al. |
| 2004/0126333 A1 | 7/2004 | Galli et al. |
| 2004/0258757 A1 | 12/2004 | Bosch et al. |
| 2005/0215639 A1 | 9/2005 | Mohr et al. |
| 2005/0232894 A1 | 10/2005 | Weiner et al. |
| 2006/0019987 A1 | 1/2006 | Fust et al. |
| 2006/0135464 A1 | 6/2006 | Johnson |
| 2007/0054834 A1 | 3/2007 | Baker |
| 2007/0248629 A1 | 10/2007 | Friden et al. |
| 2008/0026013 A1 | 1/2008 | Rabinovich-Guilatt et al. |
| 2008/0260837 A1 | 10/2008 | Namburi et al. |
| 2009/0118168 A1* | 5/2009 | Dinh et al. .................. 514/9 |
| 2009/0191288 A1 | 7/2009 | Squires |
| 2010/0075914 A1 | 3/2010 | Flack et al. |
| 2011/0076244 A1 | 3/2011 | Hammer |
| 2011/0091556 A1 | 4/2011 | Baker, Jr. et al. |
| 2012/0115812 A1 | 5/2012 | Hammer |
| 2012/0190715 A1* | 7/2012 | Johnson et al. ............ 514/358 |
| 2012/0219602 A1 | 8/2012 | Flack et al. |
| 2013/0108679 A1 | 5/2013 | Butterfield et al. |
| 2013/0123308 A1 | 5/2013 | Ghannoum et al. |
| 2013/0226107 A1 | 8/2013 | Fields |
| 2015/0045443 A1 | 2/2015 | Weaver |

FOREIGN PATENT DOCUMENTS

| | | |
|---|---|---|
| DE | 43 28 828 | 3/1995 |
| DE | 69624340 | 6/2003 |
| EP | 0175338 | 3/1986 |
| EP | 0181184 | 5/1986 |
| EP | 0190797 | 8/1986 |
| EP | 0 308 210 | 3/1989 |
| EP | 0478445 | 9/1991 |
| EP | 0487066 | 5/1992 |
| EP | 0872248 | 10/1998 |
| EP | 0937394 | 8/1999 |
| FR | 2700698 | 7/1994 |
| GB | 1479480 | 7/1977 |
| JP | 4 182431 | 6/1992 |
| JP | 61 76401 | 6/1994 |
| JP | 08 164191 | 6/1996 |
| JP | 08 217694 | 8/1996 |
| JP | 10 324624 | 12/1998 |
| WO | 94 05258 | 3/1994 |
| WO | 95 03734 | 2/1995 |
| WO | 96 24367 | 8/1996 |
| WO | 97/29742 | 8/1997 |
| WO | 97 34607 | 9/1997 |
| WO | 98/11778 | 3/1998 |
| WO | 98 18474 | 5/1998 |
| WO | 98/42188 | 10/1998 |
| WO | 99/08713 | 2/1999 |
| WO | 99 12545 | 3/1999 |
| WO | 9916447 | 4/1999 |
| WO | WO 2004019682 | 3/2004 |
| WO | WO 2004050059 | 6/2004 |

OTHER PUBLICATIONS

Neyts et al. Antimicrobial Agents and Chemotherapy (1998), vol. 42, pp. 216-222.*
Kurokawa et al. Antiviral Research (1995), vol. 27, pp. 19-37.*
U.S. Appl. No. 09/669,068, filed Sep. 22, 2000, Johnson.
U.S. Appl. No. 09/669,067, filed Sep. 22, 2000, Johnson.
U.S. Appl. No. 09/668,950, filed Sep. 22, 2000, Johnson.
U.S. Appl. No. 13/012,719, filed Jan. 24, 2011, Johnson.
AHFS Drug Information, pp. 3107-3108, 1999.
Armstrong et al., "Inactivation of Viruses by Benzalkonium Chloride", Applied Microbiology, vol. 12, No. 2, p. 132-137, Mar. 1964.
Berti, et al., Transcutaneous Drug Delivery: A Practical Review, Mayo Clin. Proc., vol. 70, pp. 581-586, Jun. 1995.

(56) References Cited

OTHER PUBLICATIONS

Choi, et al., The Pretreatment Effect of Chemical Skin Penetration Enhancers in Transdermal Drug Delivery Using Iontophoresis, Skin Pharmacol. Appl. Skin Physiol., pp. 326-335, 1999.
Comfort et al., Enhanced Transport in a Therapeutic Transdermal System, Biomaterials, vol. 11, No. 9, pp. 729-733, Nov. 1990.
Encyclopedia of Chemistry, vol. 1, Ed. Editorial Committee for Encyclopedia of Chemistry, Kyoritsu Shuppan Co., Ld., Feb. 15, 1987, p. 888. (Cited as showing the density of ethanol.).
Fang et al., Development and Evaluation on Transdermal Delivery of Enoxacin Via Chemical Enhancers and Physical Iontophoresis, Journal of Controlled Release, vol. 54, pp. 293-304, 1998.
Gismondo, et al., Efficacia Antimicrobica e Sporicida di Varie Soluzioni Disinfettanti, Minerva Medica, (Italy) vol. 86, pp. 21-32, Jan.-Feb. 1995 (English translation attached: Antimicrobial and Sporicidal Efficacy of Some Disinfectant Solutions).
James Alexander Corporation flyer, Medicaine® Topical Antiseptic, 1997.
James Alexander Corporation flyer, Medicaine® Sting and Bite Relief Formula Flyer, 1997.
James Alexander Corporation flyer, Unit Dose Swabs, 1997.
Jin et al., Effect of Application Volume of Ethanol-Isopropyl Myristate Mixed Solvent System on Permeation of Zidovudine and Probenecid Through Rat Skin, Drug Development and Industrial Pharmacy, vol. 26 No. 2, pp. 193-198, 2000.
Johnson, et al., Synergistic Effects of Chemical Enhancers and Therapeutic Ultrasound on Transdermal Drug Delivery, Journal of Pharmaceutical Sciences, vol. 85, No. 7, pp. 670-679, Jul. 1996.
Kanikkannan, et al., Structure-Activity Relationship of Chemical Penetration Enhancers in Transdermal Drug Delivery, Current Medicinal Chemistry, vol. 7, No. 6, pp. 593-608, 2000.
Kunta et al., (1997), "Effect of menthol and related terpenes on the percutaneous absorption of propranolol across excised hairless mouse skin," Journal of Pharmaceutical Sciences, 86(12), pp. 1369-1373. (Abstract only).
Martindale, The Extra Pharmacopoeia, Benzethonium Chloride/ Benzyl Alcohol, p. 1119, Royal Pharmaceutical Society, 1996.
Martindale, The Extra Pharmacopoeia, Disinfectants and Preservatives, pp. 1114-1116, Royal Pharmaceutical Society, 1996.
Martindale, The Extra Pharmacopoeia, Ethyl Hydroxybenxoate/Magenta, p. 1137, Royal Pharmaceutical Society, 1996.
Martindale, The Extra Pharmacopoeia, Local Anesthetics, pp. 1317, 1320-1321, Royal Pharmaceutical Society, 1996.
Meyler's Side Effects of Drugs, An Encyclopedia of Adverse Reactions and Interactions, Antiseptic Drugs and Disinfectants, Chapter 24, pp. 643-644 and 664-665, 1996.
Remington's Pharmaceutical Sciences, 15th Edition, 1975, Mack Publishing Co., p. 685.
Sanofi Pharmaceuticals, Inc., Zephiran® Chloride, Brand of Benzalkonium Chloride, 1997.
The Merck Index, An Encyclopedia of Chemicals, drugs, and Biologicals, Twelfth Edition, pp. 177 and 180, 1996.
Williams, et al., Skin Absorption Enhancers, Critical Reviews in Therapeutic Drug Carrier Systems, 9(3,4), pp. 305-353, 1992.
Wu et al., In Vitro Effect of Penetration Enhancers on Sodium Nonivamide Acetate in Rat Skin, Biol. Pharm. Bull., vol. 18, No. 12, pp. 1790-1792, 1995.Williams, et al., Skin Absorption Enhancers, Critical Reviews in Therapeutic Drug Carrier Systems, 9(3,4), pp. 305-353, 1992.
Zatz, Joel L., Ph.D., Enhancing Skin Penetration of Actives With the Vehicle, Cosmetics and Toiletries Magazine, Sep. 1994, vol. 109, 6 pgs, Allured Publishing Co.
Zatz, Joel L., Ph.D., Modification of Skin Permeation by Solvents, Cosmetics and Toiletries Magazine, Feb. 1991, vol. 106, 8 pgs, Allured Publishing Co.
U.S. Appl. No. 09/401,076, filed Aug. 3, 2000, Office Action.
U.S. Appl. No. 09/401,076, filed Nov. 1, 2000, Notice of Allowance.
U.S. Appl. No. 09/668,949, filed Sep. 13, 2001, Office Action.
U.S. Appl. No. 09/668,950, filed Sep. 13, 2001, Office Action.
U.S. Appl. No. 09/668,951, Sep. 21, 2001, Office Action.
U.S. Appl. No. 09/668,951, filed Feb. 26, 2002, Notice of Allowance.
U.S. Appl. No. 09/668,953, filed Sep. 25, 2001, Office Action.
U.S. Appl. No. 09/668,953, filed Mar. 4, 2002, Notice of Allowance.
U.S. Appl. No. 09/669,068, filed Feb. 26, 2002, Notice of Allowance.
U.S. Appl. No. 10/200,897, filed Aug. 20, 2003, Office Action.
U.S. Appl. No. 10/200,897, filed Jan. 16, 2004, Notice of Allowance.
U.S. Appl. No. 09/993,178, filed Mar. 26, 2002, Notice of Allowance.
U.S. Appl. No. 11/348,127, filed Oct. 4, 2007, Office Action.
U.S. Appl. No. 11/348,127, filed Feb. 29, 2008, Office Action.
U.S. Appl. No. 10/816,571, filed Nov. 28, 2007, Office Action.
U.S. Appl. No. 10/816,571, filed May 22, 2008, Office Action.
U.S. Appl. No. 10/816,571, filed Sep. 17, 2009, Office Action.
U.S. Appl. No. 10/816,571, filed Mar. 30, 2010, Office Action.
U.S. Appl. No. 10/816,571, filed Dec. 21, 2010, Office Action.
U.S. Appl. No. 10/816,571, filed Jul. 21, 2011, Office Action.
U.S. Appl. No. 10/816,571, filed Nov. 28, 2011, Office Action.
U.S. Appl. No. 10/816,571, filed Dec. 28, 2011, Notice of Allowance.
U.S. Appl. No. 13/157,210, filed Oct. 28, 2011, Office Action.
U.S. Appl. No. 13/157,210, filed Mar. 20, 2012, Notice of Allowance.
Satyaprakash et al., Viremia in Acute Herpes Zoster, JID 2009:200 (Jul. 1, 2009) pp. 26-32 Downloaded from http://jid.oxfordjournals.org/ Feb. 16, 2015.

* cited by examiner

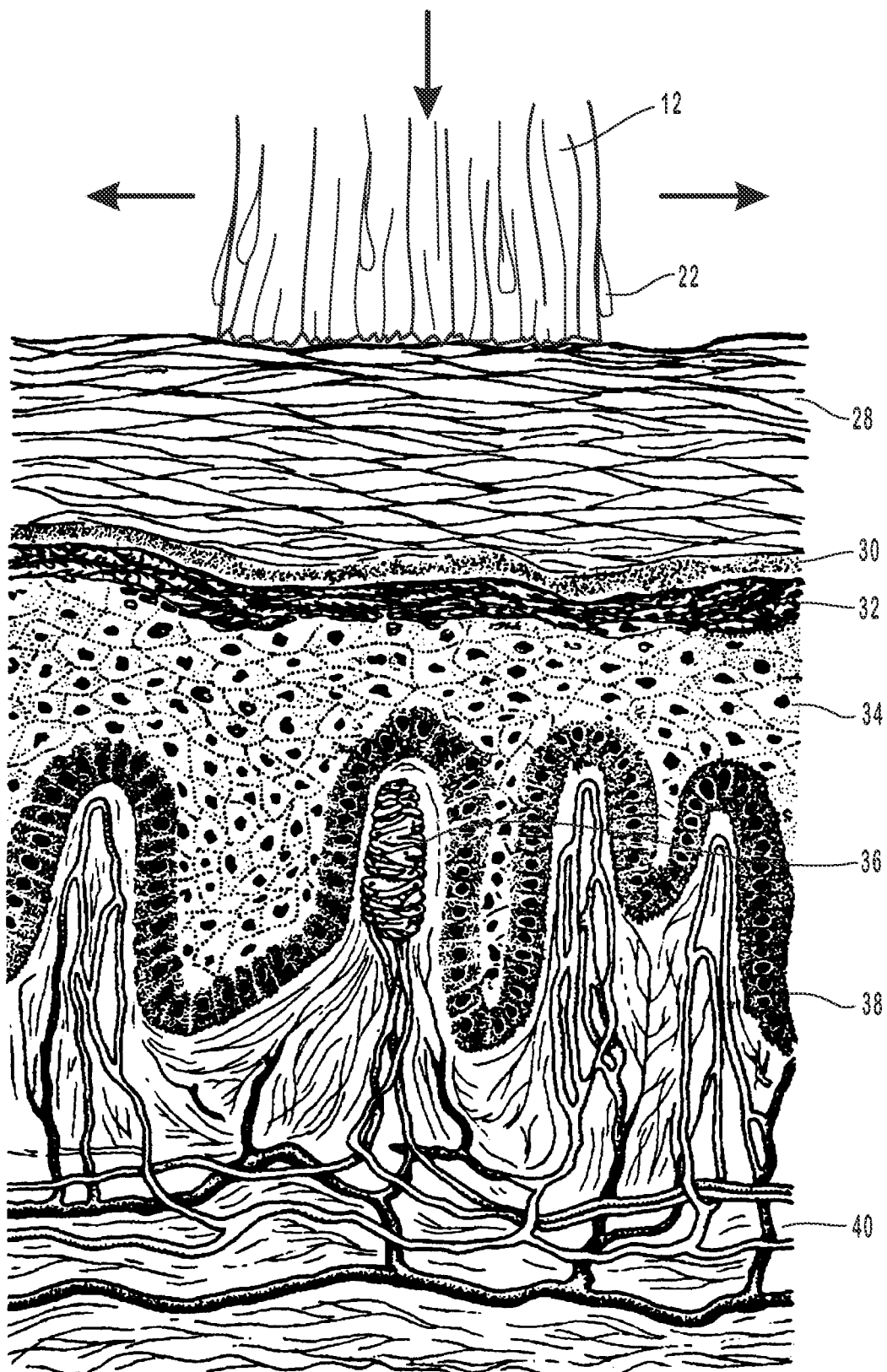

COMBINED SYSTEMIC AND TOPICAL TREATMENT OF DISORDERED TISSUES

BACKGROUND OF THE INVENTION

1. The Field of the Invention

The present invention relates to kits and methods for treating disordered tissues caused by a virus, such as herpes virus, that combine systemic and topical treatments.

2. The Relevant Technology

Tissue disorders caused by viruses, particularly those which impact epithelial tissue, include Herpes simplex virus types I and II, herpes zoster, varicella-zoster, cytomegalovirus, and HHV-8, which causes Kaposi's Sarcoma. Such viruses can cause painful, disfiguring and/or highly infectious disordered tissues (e.g., blisters or lesions), which are physically and psychologically debilitating. Disordered tissues caused by viruses are often difficult to treat and can last a lifetime.

Herpes simplex virus types I and II and herpes varicella-zoster, commonly referred to as "herpes virus" or "herpes," are infectious diseases which have reached crisis proportions nationally with estimated numbers of infected people at 70%-80% of U.S. population as reported by the American Social Health Association (ASHA) and growing annually by 500,000 people or more.

Herpes enters the human body through minuscule breaks in the epidermal tissue usually by contact with an infected host and is marked by eruption of one or more vesicles, usually in groups, following an incubation period of approximately four to ten days. Typically the course of the infectious outbreak initiates with the prodromal stage, advancing to vesicular eruption, followed by ulceration, coalescing, resolution, and latency period. The outbreak can last for several weeks and, on average, lasts two to three weeks. In some immune compromised individuals, outbreaks can last for months. The lesions caused by varicella-zoster (shingles) can last 21 days or longer. The vesicles can appear anywhere on epithelial tissues including the skin or mucosa, typically appearing on the lips as cold sores, glands, oral mucosa, conjunctiva and cornea, genitalia, anal mucosa and peri-anal tissue.

Herpes symptoms include: inguinal swelling, pain, fever, malaise, headaches, muscle aches, and swollen glands. Some individuals with oral herpes, which impacts the trigeminal nerve, have excruciating facial pain, difficulty swallowing, eating and facial swelling. Individuals with the herpes which impacts the sacral nerve have severe upper leg pain, swelling, and great difficulty walking.

Herpes is recurring, residing in the nerve ganglia, then recurring due to some, as yet unknown, stimulus mechanism. Recurrent herpetic infections can be precipitated by almost anything, including overexposure to sunlight, nutritional deficiencies, stress, menstruation, immunosuppression, certain foods, drugs, febrile illness, suppression of the immune system, and the like.

Herpes infections pose serious health threats, often causing blindness, increased cancer risk of the cervix, aseptic meningitis and encephalitis, neonatal deaths, viremia, the spread of the human immunodeficiency virus (HIV), and the like. The devastating effects of herpes diseases go well beyond the medical scope of human suffering. Herpes can be responsible for serious psychological and emotional distress as well as substantial economic loss. Other viral diseases are transmitted in different manners and may have different symptoms but can be as painful emotionally and physically to a patient.

The most common (and only FDA-approved) therapeutic treatment of herpetic or other viral disorders is through systemic treatment, such as using nucleoside analogs or other drugs that inhibit or interrupt replication of the virus causing the disorder. Systemic treatments can be taken orally or intravenously and can prevent or inhibit outbreaks. Systemic treatment generally inhibits or disrupts the reproductive cycle of the target virus. However, systemic treatments can take a significant amount of time to metabolize and convert into the active form. Once in active form, they must be delivered throughout a patient's entire body to eliminate the virus. During the time required to deliver the medication to the patient's body, the patient can still experience outbreaks that cause significant discomfort while the patient waits for the medication to take effect. In addition, the stratum basal layer can prevent medication from passing through to the epidermis so that infected regions of the epidermis continue to experience the outbreak cycle. Hence, systemic treatments may be ineffective in treating an existing outbreak of skin lesions, including the pain and discomfort experienced by the patient. Furthermore, a person can re-infect themselves by touching an infected outbreak area (even while taking a systemic medication) and exposing another area of their body with the virus.

In contrast to systemic treatments, topical treatments are intended to reduce the pain and severity associated with disordered tissues caused by herpes or other viruses. They can be soothing as a salve over the tender surface of the disordered tissue. However, they rarely if ever provide actual therapeutic treatment of the underlying cause of the disorder, which is the system-wide existence of virus in the person's body.

In view of the widespread nature of herpes and other viral caused disordered tissues, coupled with the general ineffectiveness of existing treatments, there exists an ongoing need to develop effective treatments that can shorten, reduce or eliminate outbreaks of disordered tissues.

BRIEF SUMMARY

Disclosed herein are kits and methods for treating disordered tissue caused by a virus in a human that involve co-administration of a systemic anti-virus drug and topically administering an anti-infective composition. It has now been discovered that administering an appropriate topical treatment together with a systemic anti-virus drug can synergistically work together to increase the effectiveness of the systemic treatment in order to shorten the duration of the outbreak, reduce or eliminate future outbreaks, and reduce or eliminate post-herpetic neuralgia (a condition that causes the patient to experience pain weeks, months, years, or decades after the lesions have healed).

The systemic anti-virus drug can be administered internally, such as orally or intravenously, and is designed to disrupt or inhibit virus replication within the human body. Examples include nucleoside analogues, nucleoside analogue precursors, and nucleotide analogues. The topically administered treatment is a penetrating anti-infective composition which includes at least one anti-infective agent, such as an organohalide (e.g., benzalkonium chloride) and which is formulated to penetrate below the disordered tissue surface and kill viruses at the disordered tissue site without entering the bloodstream. The anti-infective composition reduces the time and/or number of dosages of systemic anti-virus drug required to treat the disordered tissue and its underlying cause. It also reduces or eliminates nerve damage, which can cause post-herpetic neuralgia when used together with a systemic anti-viral drug.

This is surprising and unexpected since topical herpes treatments are considered to be merely temporary soothing agents rather than drugs that are systemically effective in killing viruses. It is postulated that that during an outbreak that causes disordered tissue lesions, a disproportionately large number of the viruses within the patient's body are concentrated near the skin surface at the disordered tissue site. It is further postulated that inactivating such viruses topically by administering a penetrating anti-infective composition reduces the overall number of viruses in the patient's body that must be treated by the systemic drug, thereby significantly reducing the amount of time and/or dosages of systemic anti-virus drug that would otherwise be required to treat the outbreak using the systemic drug by itself. In addition, it is postulated that, to the extent the stratum basal layer inhibits systemically administered medication from passing through to the epidermis, topically treating and deactivating viruses at the disordered tissue site may be more effective than deactivation of such viruses using a systemic treatment. The result is synergistic dual treatment of the disease by the systemic treatment, which is highly effective in treating viruses internally but less effective in treating viruses near the skin surface, coupled with topical treatment of the disordered tissue at the skin surface using a penetrating anti-infective composition, which is effective in deactivating viruses near the skin surface but not internally beyond the disordered tissue site.

Further synergy is exhibited in that co-administration of a systemic anti-viral drug and a topically administered penetrating anti-infective composition also reduces or eliminates nerve damage, which can cause Post-Herpetic Neuralgia (PHN). This is unexpected since systemic anti-viral drugs on their own can often resolve the acute symptoms associated with disordered tissues yet not prevent nerve damage and/or chronic neuralgia, which is an extremely painful neurological condition for which there is no known cure.

An example method of treating disordered tissues caused by viruses in a mammal includes: (1) internally administering an effective amount of a systemic anti-virus drug to a mammal in need thereof in order to disrupt or inhibit virus replication systemically; and (2) topically administering an anti-infective composition comprising at least one anti-infective agent to the disordered tissue in order for the composition to penetrate below the disordered tissue surface and allow the anti-infective agent to deactivate viruses at the disordered tissue site.

An example kit for use in treating disordered tissues caused by a virus in a mammal includes: (1) an effective amount of an orally administered systemic anti-virus drug that, when administered to a mammal in need thereof, disrupts or inhibits virus replication systemically; and (1) a topically administered penetrating anti-infective composition comprising an anti-infective agent and a tissue penetrating liquid carrier that promotes penetration of the anti-infective composition into the disordered tissue and below the surface so as to allow the anti-infective composition to kill viruses at the disordered tissue site.

Topically administering the anti-infective composition can reduce the duration and/or number of dosages of the systemic anti-virus drug by at least about 10% compared to treatment of the disordered tissue by the anti-virus drug alone, in the absence of co-administering an anti-infective composition topically, preferably by at least about 20%, more preferably by at least about 30%, and most preferably by at least about 40%. Co-administration of systemic and topical treatments can also reduce or eliminate post-herpetic neuralgia, which is a common symptom even after successful resolution of disordered tissue using anti-viral drugs. Moreover, the treatment may involve only 5 applications or less of the topically-applied anti-infective composition throughout the entire treatment process, preferably 3 dosages or less, more preferably 2 dosages or less, and most preferably a single dosage.

According to one embodiment, the anti-infective composition may include at least one topical anesthetic that not only reduces pain but enhances penetration of the anti-infective composition into the disordered tissue and to accelerate deactivation of viruses and healing of the disordered tissue.

This Brief Summary is provided to introduce in a simplified form a selection of concepts that are further described below in the Detailed Description. This Brief Summary is not intended to identify key or essential features of the claimed subject matter, nor is it intended to be used as an aid in determining the scope of the claimed subject matter. Additional features and advantages of the invention will be set forth in the description which follows, and in part will be evident to persons of ordinary skill in the art from the description and appended claims, or may be learned by such persons through the practice of the invention.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. It should be noted that the figures are not necessarily drawn to scale, and that elements of similar structure or function are generally represented by like reference numerals for illustrative purposes throughout the figures. These drawings depict only certain embodiments of the invention and are not therefore to be considered to be limiting of its scope.

FIG. 1 is a vertical cross-section of the epidermis and the papillae of the dermis;

DETAILED DESCRIPTION OF THE PREFERRED EMBODIMENTS

I. Introduction

The present invention is directed to methods for kits for treating disordered tissues caused by a virus, particularly those which impact epithelial tissue such as Herpes simplex virus types I and II, herpes zoster, or varicella-zoster, or HHV-8, which causes Kaposi's Sarcoma. The method generally includes (1) administering an effective amount of a systemic anti-virus drug to a mammal in need thereof in order to disrupt or inhibit virus replication systemically within the body and (2) topically administering an anti-infective composition to the disordered tissue in order for the composition to penetrate below the surface and allow the anti-infective agent to kill viruses at the disordered tissue site. Surprisingly and unexpectedly, topically administering the anti-infective composition reduces the amount of time and/or number of dosages required for the systemic anti-virus drug to treat the underlying virus disorder compared to only administering the systemic anti-virus drug by itself in the absence of topically administering the anti-infective composition.

Further synergy is exhibited in that co-administration of a systemic anti-viral drug and a topically administered penetrating anti-infective composition also reduces or eliminates nerve damage, which can cause post-herpetic neuralgia. This is unexpected since systemic anti-viral drugs on their own can often resolve the acute symptoms associated with disordered tissues yet not prevent nerve damage and/or chronic neuralgia, which is an extremely painful neurological condition for which there is no known cure.

II. Compositions for Systemic Treatment

As used herein, "systemic treatment" refers to administration of an anti-virus drug internally (i.e., inside the body) to a patient. Administration may be oral and/or parenteral (e.g., subcutaneous, intramuscular, intravenous, intradermal, intrathecal and/or epidural administration). Systemic treatments generally affect the body on a system-wide basis rather than on a local level. Systemic compositions may include one or more components comprising active agents, carriers and/or therapeutic components, as will now be described.

A. Active Agent for Systemic Treatments

The active agents of the systemic compositions can include one or more anti-virus drugs. Such drugs act to disrupt or inhibit the replication of herpes and herpes-related viruses. Examples of anti-virus drugs that are useful for systemic treatments include nucleoside analogues, nucleoside analogue precursors, and nucleotide analogues, which mimic nucleosides or nucleotides required for virus replication but are not the actual nucleosides or nucleotides required for successful or healthy virus replication. Examples of nucleoside analogues include, but are not limited to, aciclovir (alternatively spelled "acyclovir") (acycloguanosine) (2-Amino-1,9-dihydro-9-((2-hydroxyethoxy)methyl)-6H-purin-6-one) (alternatively spelled "acyclovir"), penciclovir (2-amino-9-[4-hydroxy-3-(hydroxymethyl)butyl]-6,9-dihydro-3H-purin-6-one) (sold under the trademark Denavir®), famciclovir (2-[Racetyloxy)methyl]-4-(2-amino-9H-purin-9-yl)butyl acetate) (sold under the trademark Famvir®), idoxuridine (1-[R2R,4S,5R)-4-hydroxy-5-(hydroxymethyl)oxolan-2-yl]-5-iodo-1,2,3,4-tetrahydropyrimidine-2,4-dione), ganciclovir (2-amino-9-{[(1,3-dihydroxypropan-2-yl)oxy]methyl}-6,9-dihydro-3H-purin-6-one) (sold under the trademark Cytovene®), cidofovir (({[(S)-1-(4-amino-2-oxo-1,2-dihydropyrimidin-1-yl)-3-hydroxypropan-2-yl]oxy}methyl)phosphonic acid) (sold under the trademark Vistide®), and derivatives thereof.

An example of a nucleoside analogue precursor (i.e., which is converted into the nucleoside analogue aciclovir in vivo) includes valaciclovir (S)-2-[(2-amino-6-oxo-6,9-dihydro-3H-purin-9-yl)methoxy]ethyl-2-amino-3-methylbutano ate) (sold under the trademark Valtrex®) and derivatives thereof. Examples of nucleotide analogues include, but are not limited to, adefovir ({[2-(6-amino-9H-purin-9-yl)ethoxy]methyl}phosphonic acid) (sold under the trademark Hepsera®), tenofovir (({[(2R)-1-(6-amino-9H-purin-9-yl)propan-2-yl]oxy}methyl)phosphonic acid) (sold under the trademark Viread®), and derivatives thereof.

Also contemplated are inhibitors of herpesvirus DNA replication (e.g., 4-oxo-dihydroquinones), possible inhibitors of herpesvirus gene expression (e.g., fomivirsen, pyrazoloquinoline, and benzothiophene), inhibitors of herpesvirus assembly, encapsidation and nuclear egress (e.g., acridones, thiourea inhibitors, phenylenediamine-sulfonamides, and ribosylbenzimazoles), inhibitors of cellular proteins that block viral replication (e.g., CDK inhibitors, such roscovitine) and cyclooxygenase inhibitors (e.g., BMS-279652, BMS-279654, BMS-279655), and forscarnet (phosphonoformic acid).

Aciclovir has been widely studied for its anti-viral properties. The chemical formulation of acyclovir is 9-(2-hydroxyethoxymethyl)guanine, which has the structure:

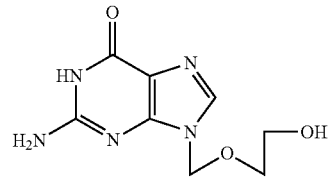 [SMILES: Nc1nc2c(ncn2COCCO)c(=O)[nH]1]

Aciclovir phosphate derivatives can also be used in systemic compositions, examples of which include:
aciclovir monophosphate (ACV-MP);
aciclovir diphosphate (ACV-DP);
aciclovir monophosphate glycerol (ACV-MP-G);
aciclovir diphosphate glycerol (ACV-DP-G);
aciclovir monophosphate morpholidate (ACV-MP-morpholine);
aciclovir monophosphate isopropylidene glycerol (ACV-MP-isoP-G); and
aciclovir diphosphate isopropylidene glycerol (ACV-DP-isoP-G).

Methods for making the above aciclovir phosphate derivatives are taught in U.S. Pat. No. 5,580,571, herein incorporated by reference.

Other aciclovir derivatives can be formed from purinyl and pyrimidinyl tetrahydrofurans to enhance anti-viral activity. These derivatives can include:

3R-(3α,4β,5α)]-2-Amino-1,9-dihydro-9-tetrahydro-4-hydroxy-5-(hydroxymethyl)-3-furanyl]-6H-purin-6-one;

[2R-[2α(S*),3α,4β]]-Tetrahydro-β,3,4-trihydroxy-2-furanethanol;

[2S-(2α,3α,4β)]-Tetrahydro-3,4-dihydroxy-2-furancarboxaldehyde;

[2R-(2α,3α,4β)]-Tetrahydro-3,4-dihydroxy-2-furanmethanol;

[4aα-(4aα,7α,7aα)]-Tetrahydro-2,2-dimethyl-4H-furo[3,2-d]-1,3-dioxin-7-ol;

[4aα-(4aα,7α,7aα)]-Tetrahydro-2,2-dimethyl-4H-furo[3,2-d]-1,3-dioxin-7-ol, acetate ester;

[2R-(2α,3α,4β)]-Tetrahydro-3,4-dihydroxy-2-furanmethanol, 4-acetate ester;

[2R-(2α,3α,4β)]-Tetrahydro-2-[[(4-methoxyphenyl)diphenylmethoxy]methyl]-3,4-furandiol, 4-acetate ester;

[2R-(2α,3α,4β)]-Tetrahydro-2-[[(4-methoxyphenyl)diphenylmethoxy]methyl]-3,4-furandiol, 4-acetate, 3-methanesulfonate ester;

[2R-(2α,3β,4β)]-3,4-Epoxytetrahydro-2-[[(4-methoxyphenyl)diphenylmethoxy]methyl]furan;

3R-(3α,4β,5β]-6-(phenylmethoxy)-9-tetrahydro-4-hydroxy-5-[[(4-methoxyphenyl)diphenylmethoxy]methyl]-3-furanyl]-9H-purin-2-amine;

[3R-(3α,4β,5α)]-2-Amino-1,9-dihydro-9-tetrahydro-4-hydroxy-5-(hydroxymethyl)-3-furanyl]-6H-purin-6-one;

[3-(3α,4β,5α)]-5-Methyl-1-[tetrahydro-4-hydroxy-5-(hydroxymethyl)-3-furanyl]2,4(1H,3H)pyrimidinedione;

[2R-[2α(S*),3α,4β]]-Tetrahydro-β,3,4-trihydroxy-2-furanethanol;

[4aR(4aα,7α,7aα)]-Tetrahydro-2,2-dimethyl-4H-furo[3,2-d]-1,3-dioxin-7-ol;

[4aR-(4aα,7α,7aα)]-Tetrahydro-2,2-dimethyl-4H-furo[3,2-d]-1,3-dioxin-7-ol, acetate ester;

[2R-(2α,3α,4β)]-Tetrahydro-3,4-dihydroxy-2-furanmethanol, 4-acetate ester;

[2R-(2α,3α,4β)]-Tetrahydro-2-[(4-methoxyphenyl)diphe-nylmethoxy]methyl]-3,4-furandiol, 4-acetate ester;
2R-(2α,3α,4β)]-Tetrahydro-2-[[(4-methoxyphenyl)diphe-nylmethoxy]methyl]-3,4-furandiol, 4-acetate, 3-methane-sulfonate ester;
[2R-(2α,3β,4β)]-3,4-Epoxytetrahydro-2-[[(4-methoxyphe-nyl)diphenylmethoxy]-methyl]furan;
[3R-(3α,4β5α)]-5-Methyl-1-[tetrahydro-4-hydroxy-5-[[(4-methoxyphenyl)diphenylmethoxy]methyl]-3-furanyl]-2,4 (1H,3H)pyrimidinedione;
[3R-(3α,4β,5α)]-5-Methyl-1[tetrahydro-4-hydroxy-5-(hy-droxymethyl)-3-furanyl]-2,4-(1H,3H)pyrimidinedione;
[3R-(3α,4β,5α)]-4-Amino-1-[tetrahydro-4-hydroxy-5-(hy-droxymethyl)-3-furanyl]-2(1H)-pyrimidinone;
[3R-(3α,4β,5α)]-4-Amino-1-[tetrahydro-4-hydroxy-5-[[(4-methoxyphenyl)diphenylmethoxy]methyl]-3-furanyl]-2 (1H)-pyrimidinone;
3R-(3α,4β,5α)]-4-Amino-1-[tetrahydro-4-hydroxy-5-(hy-droxymethyl)-3-furanyl]-2(1H)-pyrimidinone;
[3R-(3α,4β,5α)]-1-[Tetrahydro-4-hydroxy-5-(hydroxym-ethyl)-3-furanyl]-2,4(1H,3H)pyrimidinedione;
[2R-(2α,3β,4β)]Tetrahydro-2-[(triphenylmethoxy)methyl]-3,4-furandiol;
[3aR-(3aα,4α,6aα)]-Tetrahydro-4-[(triphenylmethoxy)me-thyl]furo[3,4-d]-1,3,2-dioxathiole, 2,2-dioxide;
[3R-(3α,4β,5α)]-1-[Tetrahydro-4-hydroxy-5-[(triphenyl-methoxy)methyl]-3-furanyl]-2,4(1H,3H)-pyrimidinedi-one; and
[3R-(3α,4β,5α)]-1-Tetrahydro-4-hydroxy-5-(hydroxym-ethyl)-3-furanyl]-2,4(1H,3H)pyrimidinedione.

Methods for producing pharmaceutically acceptable formu-lations of the above aciclovir derivatives are taught in U.S. Pat. No. 5,272,152, herein incorporated by reference.

In one embodiment, the active agent is an amino acid ester of aciclovir. Amino acid esters of aciclovir include glycine, alanine, valine esters. For example, the valine ester of aciclo-vir, also referred to as valaciclovir), has been shown in U.S. Pat. No. 4,957,924, herein incorporated by reference, to have improved bioavailability in oral administration. Valaciclovir can be converted to aciclovir and are thus analogs of each other. Further, aciclovir is a metabolite of valaciclovir in that valaciclovir may also be converted to aciclovir during internal metabolization and distributions thereof. The chemical for-mula of valaciclovir is 2-(2-amino-1,6-dihydro-6-oxo-(H (purin-9-yl)methyxy)ethyl L-valinate, which has the struc-ture:

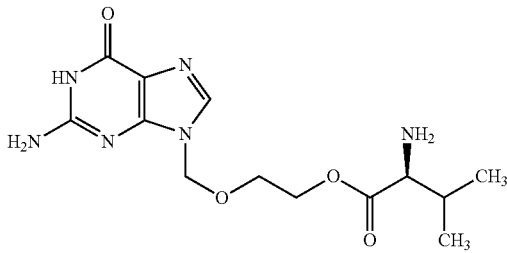 [SMILES: CC(C)[C@H](N)C(=O)OCCOCn1cnc2c(=O)[nH]c(N)nc21]

Also contemplated are pharamacuetically acceptable salts thereof. Suitable valaciclovir derivatives include:
2-[(2-Amino-1,6-dihydro-6-oxo-9H-purin-9-yl)methoxy] ethyl N-[(benzyloxy)carbonyl] L-valinate;
2-[(2-Amino-1,6-dihydro-6-oxo-9H-purin-9-yl)methoxy] ethyl L-valinate;
2-(2-Amino-1,6-dihydro-6-oxo-9H(purin-9-yl)methoxy) ethyl L-valinate hydrochloride monohydrate;
2-[(2-Amino-1,6-dihydro-6-oxo-9H-purin-9-yl)methoxy] ethyl N-[(benzyloxy)carbonyl] L-valinate; and
2-[(2-Amino-1,6-dihydro-6-oxo-9H-purin-9-yl)methoxy] ethyl L-valinate hydrochloride monohydrate.

Methods for producing pharmaceutically acceptable formu-lations of valaciclovir and pharamacuetically acceptable salts thereof are described in U.S. Pat. No. 4,957,924, herein incor-porated by reference.

Penciclovir is another derivative of aciclovir. The chemical formula of penciclovir is 9-[4-Hydroxy-3-(hydroxymethyl) butyl]guanine, which has the chemical structure:

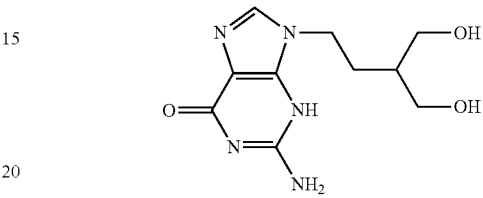

Also contemplated are pharmaceutically acceptable salts, phosphate ester, or acyl derivative thereof. Example deriva-tives are where the oxo group is replaced with chlorine, straight or branched chain $C_{1-6}$ alkoxy, preferably methoxy, phenoxy, phenyl $C_{1-6}$ alkoxy, $NH_2$, —OH or —SH, with the proviso that when the oxo group is replaced with —OH, the compound of penciclovir is in a purity state of greater than 50% by weight of pure compound. Suitable derivatives of penciclovir include:
2-Amino-1,9-dihydro-9-[4-hydroxy-3-(hydroxymethyl) but-1-yl]-6H-purine;
5-(2-Hydroxyethyl)-2,2-dimethyl-1,3-dioxan;
5-(2-Bromoethyl)-2,2-dimethyl-1,3-dioxan;
2-Amino-6-chloro-9-[2-(2,2-dimethyl-1,3-dioxan-5-yl) ethyl]-purine;
9-(4-Hydroxy-3-hydroxymethyl)but-1-yl)guanine;
Ethyl 4-benzyloxy-2-ethoxycarbonylbutanoate;
4-Benzyloxy-2-hydroxymethylbutan-1-ol;
2-Acetoxymethyl-4-benzyloxybut-1-yl acetate;
2-Acetoxymethyl-4-hydroxybut-1-yl acetate;
2-Acetoxymethyl-4-bromobut-1-yl acetate;
9-(4-Acetoxy-3-acetoxymethylbut-1-yl)-2-amino-6-chloro-purine;
7-(4-Acetoxy-3-acetoxymethylbut-1-yl)-2-amino-6-chloro-purine;
9-(4-Hydroxy-3-hydroxymethylbut-1-yl)guanine, sodium salt;
9-(4-Hydroxy-3-hydroxymethylbut-1-yl)guanine, potassium salt;
2-Amino-6-chloro-9-(4-hydroxy-3-hydroxymethylbut-1-yl) purine hydrochloride;
2-Amino-9-(4-hydroxy-3-hydroxymethylbut-1-yl)-6-meth-oxypurine;
2-Amino-6-ethoxy-9-(4-hydroxy-3-hydroxymethylbut-1-yl) purine;
2-Amino-6-benzyloxy-9-(4-hydroxy-3-hydroxymethylbut-1-yl) purine;
2-Amino-9-(4-hydroxy-3-hydroxymethylbut-1-yl)-6-thi-opurine;
2-Amino-6-azido-9-[2-(2,2-dimethyl-1,3-dioxan-5-yl) ethyl]-purine;
2,6-Diamino-9-[2-(2,2-dimethyl-1,3-dioxan-5-yl)ethyl]pu-rine;
2,6-Diamino-9-(4-hydroxy-3-hydroxymethylbut-1-yl)pu-rine;

9-(4-Acetoxy-3-acetoxymethylbut-1-yl)guanine;
9-(4-Propionyloxy-3-propionyloxymethylbut-1-yl)guanine;
$N^2$-Propionyl-9-(4-propionyloxy-3-propionyloxymethyl-but-1-yl)guanine;
9-(4-Hexanoyloxy-3-hexanoyloxymethylbut-1-yl)guanine;
9-(4-Formyloxy-3-formyloxymethylbut-1-yl)guanine;
9-[4-(N-Imidazolylcarbonyloxy)-3-(N-imidazolylcarbonyloxymethyl)-but-1-yl]guanine;
$N^2$-Monomethoxytrityl-9-(4-monomethoxytrityloxy-3-hydroxymethylbut-1-yl)guanine;
$N^2$-Monomethoxytrityl-9-(4-hydroxy-3-hydroxymethylbut-1-yl)-guanine;
9-(4-Pivalyloxy-3-pivalyloxymethylbut-1-yl)guanine;
9-(4-Acetoxy-3-hydroxymethylbut-1-yl)guanine;
9-(4-Benzoyloxy-3-hydroxymethylbut-1-yl)guanine;
9-(4-Hexanoyloxy-3-hydroxymethylbut-1-yl)guanine;
9-(4-Hexadecanoyloxy-3-hydroxymethylbut-1-yl)guanine;
9-(4-Hydroxy-3-hydroxymethylbut-1-yl)guanine 4'-phosphate diammonium salt;
$N^2$-Acetyl-9-(4-hydroxy-3-hydroxymethylbut-1-yl)guanine;
$N^2$-Hex anoyl-9-(4-hydroxy-3-hydroxymethylbut-1-yl)guanine;
2-Amino-9-(4-hydroxy-3-hydroxymethylbut-1-yl)-6-isopropoxypurine; and
2-Amino-9-(4-hydroxy-3-hydroxymethylbut-1-yl)-6-phenoxypurine.

Methods for producing pharmaceutically acceptable formulations of penciclovir and derivatives are described in detail in U.S. Pat. No. 5,075,445, herein incorporated by reference.

Famciclovir is another derivative of aciclovir and can be converted to penciclovir. The chemical formula for famciclovir is 9-(4-hydroxy-3-hydroxymethylbutyl)guanine, which has the chemical structure:

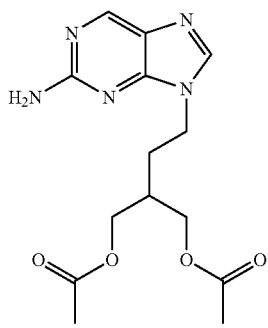 [SMILES: CC(=O)OCC(CCn1cnc2cnc(N)nc21)COC(C)=O]

Also contemplated are pharamacuetically acceptable salts thereof as well as derivatives of famciclovir. Suitable derivatives of famciclovir include:
2-amino-9-(4-hydroxy-3-hydroxymethylbut-1-yl)purine;
2-amino-9-(4-acetoxy-3-acetoxymethylbut-1-yl)purine;
2-amino-9-(4-acetoxy-3-hydroxymethylbut-1-yl)purine;
2-amino-9-(3-hydroxymethyl-4-methoxycarbonyloxybut-1-yl)purine;
2-amino-9-[2-(2,2-dimethyl-1,3-dioxan-5-yl)ethyl]purine;
2-amino-9-(4-propionyloxy-3-propionyloxymethylbut-1-yl)purine;
2-amino-9-(4-butyryloxy-3-hydroxymethylbut-1-yl)purine;
2-amino-9-(4-benzoyloxy-3-hydroxymethylbut-1-yl)purine;
2-amino-9-(4-hydroxy-3-hydroxymethylbut-1-yl)purine 4'-phosphate; and
2-amino-9-(4-hydroxy-3-hydroxymethylbut-1-yl)purine 4':4"phosphate.

Methods for producing pharmaceutically acceptable formulations of famciclovir and derivatives thereof are described in U.S. Pat. No. 5,246,937, herein incorporated by reference.

In addition, U.S. Pat. No. 5,580,571, incorporated by reference, teaches that the following nucleoside analogues exhibit enhanced anti-viral activity as phosphate esters and can be used as active agents:
1-beta-D-arabinofuranosyl-E-5-(2-bromovinyl)uracil [broavir; BV-araU];
2'-fluorocarbocyclic-2'-deoxyguanosine;
6'-fluorocarbocyclic-2'-deoxyguanosine;
1-(beta-D-arabinofuranosyl)-5(E)-(2-iodovinyl)uracil;
SQ 34,514;
HOE 602;
trifluorothymidine;
9-[(1,3-dihydroxy-2-propoxy)methyl]guanine;
5-ethyl-2'-deoxyuridine;
E-5-(2-bromovinyl)-2'-deoxyuridine;
5-(2-chloroethyl)-2'-deoxyuridine;
1-(2-deoxy-2-fluoro-beta-D-arabinofuranosyl)-5-iodocytosine (FIAC);
1-(2-deoxy-2-fluoro-beta-D-arabinofuranosyl)-5-iodouridine (FIAU);
buciclovir;
6-deoxyacyclovir;
9-(4-hydroxy-3-hydroxymethylbut-1-yl)guanine;
E-5-(2-iodovinyl)-2'-deoxyuridine;
5-vinyl-1-beta-D-arabinofuranosyluracil (V-araU);
1-beta-D-arabinofuranosulthymine (Ara-T);
2'-nor-2'deoxyguanosine (2' NDG);
9-(4-hydroxy-3-hydroxymethylbut-1-yl)guanine (penciclovir, BRL 3912); and
1-beta-D-arabinofuranosyladenine (Ara-A; vidarabine).

It will be appreciated that each of these nucleoside analogues or derivatives thereof can be an active agent in a systemic composition. The nucleoside analogues can be converted to active forms through metabolic pathways. The active agent may thus be any of the above-cited nucleoside analogues, other analog, derivative, or metabolite thereof in order to provide an active form of the active agent.

The active agent is preferably in a state which is able to be mixed with a suitable carrier. Aciclovir, in particular, is poorly soluble in water, which limits formulation of a topical solution and/or systemic treatments in aqueous carriers. In addition, aciclovir is poorly absorbed from the gastrointestinal tract after oral administration and is therefore typically be administered in large doses. Therefore, pharmaceutically acceptable formulations of nucleoside analogues can provide the drug in a form which is easily absorbed into the blood stream. A pharmaceutically acceptable salt, phosphate ester or acyl derivative of the active agent can be formulated for use as a systemic treatment, optionally with a carrier or excipient (discussed below). For example, the nucleoside analogue can be provided in a salt form which allows it to be more easily soluble in water and/or plasma. In addition, the nucleoside analogue in salt form can be more easily absorbed by the gastrointestinal tract. A pharmaceutically acceptable salt form of the active agent can thus be prepared using sodium, potassium, ammonium, or hydrogen. In addition, salt forms of active agents can be formed using hydrochloric acid, sulphuric acid, phosphoric acid, maleic acid, fumaric acid, citric acid, tartaric acid, lactic acid, acetic acid or p-toluenesulphonic acid.

In another embodiment, the active agent could be an agent, other than a nucleoside or nuclueotide analogue, which impairs the reproductive function of the virus through other mechanisms besides imitating nucleoside or nucleotides essential for replication. For example, the active agent may prevent the virus from entering the cell, which is vital for virus replication.

The amount of active agent present in the formulation should be sufficient to be antivirally effective and be non-toxic. Because nucleoside analogues, nucleoside analogue precursors, and nucleotide analogues are known in the art, one or ordinary skill can determine a pharmaceutically acceptable dosage of active agent. The desired dose can be administered as two, three, four or more sub-doses at appropriate intervals throughout the day. These sub-doses may be administered in unit dosage forms, for example, containing 10 to 1000 mg, preferably 20 to 500 mg and most preferably 100 to 400 mg of active agent per unit dosage form.

B. Carriers and Therapeutic Components for Systemic Treatment

Suitable methods for delivering the active agent systemically include, but are not limited to, oral and parenteral (including subcutaneous, intramuscular, intravenous, intradermal, intrathecal and epidural). The preferred route can vary depending on the condition of the patient. The amount delivered will depend on the severity of the condition, which can be determined by the attendant physician.

While it is possible for the active agents to be administered alone, it is preferable to present them as pharmaceutical formulations. The formulations comprise at least one active agent together with one or more carriers and optionally other therapeutic components. Preferably, the carrier is compatible with the other components of the formulation and not deleterious to the patient receiving the treatment.

The formulations may conveniently be presented in unit dosage form and may be prepared by any of the methods well known in the art of pharmacy. Such methods include the step of bringing into association the active agent with the carrier, which constitutes one or more accessory components. In general, the formulations are prepared by uniformly and intimately bringing into association the active agent with liquid carriers or finely divided solid carriers or both, and then, if necessary, shaping the product.

Formulations of systemic treatments suitable for oral administration may be presented as discrete units such as capsules, cachets or tablets each containing a predetermined amount of the active agent; as a powder or granules; as a solution or a suspension in an aqueous liquid or a non-aqueous liquid; or as an oil-in-water liquid emulsion or a water-in-oil liquid emulsion. The active agent may also be presented as a bolus, electuary, paste, gelatin capsule, or syrup. Additional flavoring or coloring components may optionally be added.

A tablet may be made by compression or molding, optionally with one or more accessory components. Compressed tablets may be prepared by compressing in a suitable machine the active agent in a free-flowing form such as a powder or granules, optionally mixed with a binder, lubricant, inert diluent, preservative, surface active or dispersing agent.

For example, magnesium stearate, starch, lactose, glucose, rice, flour and chalk may be used to form tablets. Molded tablets may be made by molding in a suitable machine a mixture of the powdered compound moistened with an inert liquid diluent. The tablets may optionally be coated or scored and may be formulated so as to provide slow or controlled release of the active agent therein.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Formulations for intramuscular administration are also contemplated.

Additionally, other therapeutic components can be used in combination with the active agent. In one embodiment, therapeutic components which enhance the anti-viral activity of the nucleoside can also be added. For example, in one embodiment, a ribonucleotide reductase (RR) inhibitor can be used on conjunction with acyclovir to provide an enhanced antiviral effect as taught in U.S. Pat. No. 4,758,572, herein incorporated by reference. In another embodiment, interferon can optionally be used.

III. Anti-Infective Compositions for Topical Administration

The terms "topical treatment" and "topical administration" refer to administration of an anti-infective composition to the surface of the disordered tissue caused by a virus. In general, the anti-infective composition is formulated and/or applied in a manner so that a therapeutically effective amount of anti-infective agent does not enter the bloodstream of the patient and therefore is not a systemic treatment (only minor, non-therapeutic amounts may be able to enter the bloodstream). Topical treatment includes external application of an anti-infective composition to disordered tissue even if located inside a body cavity (e.g., mouth, anus or vagina). Anti-infective compositions may include one or more components comprising active agents, carriers and/or therapeutic components, as will now be described.

According to one embodiment, the active agent included in the anti-infective compositions comprises at least one of an organohalide, docosanol, iodine, nucleoside analogue, or nucleotide analogue in a liquid carrier having a tissue penetrating component. Organohalides, such as quaternary ammonium halides, contain at least one carbon-halogen bond. Benzalkonium chloride is an example organohalide. Other organohalides include organo-bromides and organo-iodides. Preferably, the organohalides have an alkyl group attached thereto such as a simple $C_nH_{2n+1}$ chain, where n is in a range from 1 to about 50.

The generic chemical structure of benzalkonium chloride is shown below:

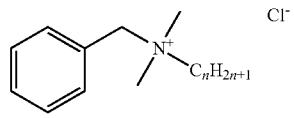

$n = 8, 10, 12, 14, 16, 18$

As shown, benzalkonium chloride includes a benzene ring and a nitrogen constituent (i.e., a quaternary ammonium group) near the ring. A carbon atom is disposed between the nitrogen constituent and the benzene ring. Two methyl groups and an alkyl group of varying size extend from the nitrogen atom.

An example embodiment includes a mixture of compounds with an alkyl chain length distribution that is about 40% $C_{12}$, about 50% $C_{14}$, and about 10% $C_{16}$ (CAS Reg. No. 68424-85-1). Examples include Maquat MC-1412-50%, Mason Chemical Company, 50% activity; Maquat MC-1412-80%, Mason Chemical Company, 80% activity; and BTC-835, Stepan Company, 50% activity. Notwithstanding the fact that "benzalkonium chloride" often refers to mixtures of compounds of varying alkyl chain length, it should be understood that one may utilize a singular benzalkonium chloride compound comprising only one alkyl chain of a particular length.

These anti-infective agents, particularly benzalkonium chloride, are highly effective in deactivation of viruses or otherwise limiting the source of infections and other complications related to disordered tissue. Also, these anti-infective agents can neutralize or eliminate toxins and inflammatory agents caused by viruses. Rapidly eliminating or neutralizing toxins, inflammatory agents, and their sources results in prompt pain relief.

Benzalkonium bromide and benzalkonium iodide are additional examples of suitable organohalides. Benzalkonium bromide has the structure of benzalkonium chloride with the difference being that the chlorine is substituted with a bromine constituent. Analogous considerations apply to benzalkonium iodide. Another example of a suitable organohalide is cetyl trimethylammonium bromide.

Examples of other organochlorides which have anti-infective properties include benzethonium chloride, methyl benzethonium chloride, cetyl pyridinium chloride, chloroxylenol, hexachlorophene, triclosan, and chlorhexidine. Note that some of the above organochlorides are not suitable for all purposes. For example, benzethonium chloride, chloroxylenol, and chlorhexidine should not be used in a manner which would enable them to be ingested in a toxic quantity. Examples of other organohalides which may be suitable, more particularly quaternary ammonium halides having an alkyl with 6-18 carbons, include: alkyl benzyl dimethyl ammonium halide, alkyl dimethyl ethyl benzyl ammonium halide, n-alkyl dimethyl benzyl ammonium halide, diisobutyl phenoxy ethoxy ethyl dimethyl benzyl ammonium halide, n-($C_{12}C_{14}C_{16}$) alkyl dimethyl benzyl ammonium halide, dodecyl dimethyl ammonium halide, dioctyl dimethyl ammonium halide, dialkyl dimethyl ammonium halide, dialkyl methyl benzyl ammonium halide, octyl decyl dimethyl ammonium halide, lauryl dimethyl benzyl ammonium halide, o-benzyl-p-chlorophenol, dideryl dimethyl ammonium halide, dioctyl dimethyl ammonium halide, and alkyl ($C_{14}C_{12}C_{16}$) dimethyl benzyl ammonium halide.

Additional examples of effective organohalides include dual quaternary ammonium compounds comprising at least two quaternary ammonium compounds, e.g., a mixture of n-alkyl dimethyl benzyl ammonium halide and n-dialkyl methyl benzyl ammonium halide. An example is distributed by Stepan as BTC7 776, with a chain length distribution for the n-alkyl of about 60% $C_{14}$, about 30% $C_{16}$, about 5% $C_{12}$, and about 5% $C_{18}$ (CAS Reg. No. 683991-10-5), and a chain length distribution for the n-dialkyl of about 60% $C_{14}$, about 30% $C_{16}$, about 5% $C_{12}$, and about 5% $C_{18}$ (CAS Reg. No. 68391-05-9). Another example comprises a mixture of n-alkyl dimethyl benzyl ammonium halide (I) and n-alkyl dimethyl ethyl benzyl ammonium halide (II). An example is distributed by Stepan as BTC 21257M series with a chain length distribution for the n-alkyl in entity (I) of about 60% $C_{14}$, about 30% $C_{16}$, about 5% $C_{12}$, and about 5% $C_{18}$ (CAS Reg. No. 683991-10-5), and a chain length distribution in entity (II) of about 68% $C_{12}$, and about 32% $C_{14}$ (CAS Reg. No. 68956-79-6).

The liquid carrier preferably has properties that enhance the ability of the treatment composition to penetrate into the disordered epithelial tissue. The carrier may have a viscosity and/or density which is not significantly greater than that of water in order to optimally enable the treatment composition to penetrate into the disordered tissue. Using a carrier composition having a viscosity which is not significantly greater than water is in contrast to compositions that are coated onto afflicted tissue. Accordingly, treatment compositions according to some embodiments exclude formulations which may be considered to be primarily or essentially gels, creams, lotions, oils, ointments, pastes, emulsions, and viscous colloidal suspensions. Alternatively, topical compositions can also include formulations which may be considered to be primarily or essentially gels, creams, lotions, oils, ointments, pastes, emulsions, and colloidal suspensions. In addition, small amounts of inert abrasive material may be present in the topical compositions.

Although, water alone may be used as the carrier, it is not preferred because other compounds, such as some alcohols, have a tissue penetrating capability that water lacks. The carrier in the topical composition is also preferably not formed entirely from an alcohol such as isopropyl alcohol or ethyl alcohol, since their use may be more painful in some circumstances. When an open sore is part of the disordered tissue, the amount of alcohol or other composition that has a significant tissue penetrating ability may be modified by adding water so as to moderate the amount of discomfort that the patient experiences by the application of the composition to the open sore. Additionally, alcohols such as isopropyl alcohol rapidly evaporate. Further, it may be preferred to use alcohols such as isopropyl alcohol with other constituents such as water due to regulatory issues. Suitable alcohols include, but are not limited to, ethanol, methanol, benzyl alcohol, cetyl alcohol, Other compounds that are preferred as carriers include acetic compounds such as acetone, acetic acid, acetic anhydride, and the like. While some acetic compounds may not be as effective as some alcohols, acetone exhibits an effective ability to penetrate tissue. In another embodiment, the carrier may include a mixture of water, alcohol, and acetone. U.S. Pat. No. 6,211,243, hereby incorporated by reference, describes suitable concentrations of water and alcohol mixtures and carriers including acetic compounds.

The carrier preferably has a tissue penetrating component, such as isopropyl alcohol, that is capable of penetrating the skin and cells in a rapid manner without rapidly diffusing beyond the skin and into the bloodstream. The treatment composition enables the stratum spinosum of skin to be saturated in the region of the cold sore or other disordered tissue for a period that enables the treatment composition to achieve its purpose before it diffuses into the body. In this way, the treatment composition forms a temporary reservoir (or bath) in the region where it is needed most. In this way, the treatment composition can maximize its effect of deactivating viruses within the disordered tissue while minimizing possible damage to surrounding healthy tissues or the organism as a whole.

While isopropyl alcohol is a preferred carrier, other alcohols may also be used. In addition to isopropyl alcohol, ethanol and methanol are also suitable carriers. Benzyl alcohol can be used as a carrier or as an additive as it also acts as a bacteriostat and an anesthetic. Acetone can also be used. Mixtures of the above-mentioned solvents may also be used as desired depending upon the application. As indicated above, however, isopropyl alcohol or ethyl alcohol is preferably used in combination with other carrier constituents. For example, as mentioned above, water may be added to isopropyl alcohol to reduce the pain which may be felt when only isopropyl alcohol is used. Similarly, isopropyl alcohol may be utilized with cetyl alcohol or a combination of cetyl, stearyl, myristyl, or lauryl alcohol and water to reduce pain. Examples of dermal penetration enhancers include dimethylsulphoxide (DMSO) and related analogues.

Carriers that include isopropyl alcohol and water can have varying ratios depending on the intended use. However, for treating colds sores, water is preferably included in a range from about 10% to about 50% by volume of the carrier, with the remainder being isopropyl alcohol. The water content is more preferably in a range from about 20% to about 40% by volume of the carrier, and most preferably about 30% by volume of the carrier and wherein the isopropyl alcohol is included in an amount of about 70%. Embodiments of preparations according to the present invention may include a carrier that comprises an alcohol, preferably isopropyl alcohol, at a concentration in a range from about 20% to about 90% by volume, preferably in a range from about 40% to about 85% by volume, and more preferably in a range from about 50% to about 80% by volume. The carrier may also include other solvents such as acetone, and the like.

A preferred method of preparing an example treatment composition involves taking 70% isopropyl rubbing alcohol USP (70% isopropanol, v/v, specific gravity 0.877 at 20 C, see 35 USP, p. 357) and then admixing the benzalkonium halide, NF. Isopropyl alcohol USP (IPA) is available from any number of US sources, including Union Carbide, Aldrich Chemical, Texaco, and Shell. Purified water USP is available from a variety of laboratory supply houses, such as Aldrich Chemical, Fisher Scientific, and VWR Scientific. Purified water USP can also be obtained by means of a commercially available water purification system designed to meet the requirements of Purified Water USP.

Embodiments include preparations with organohalide concentrations in the range from about 0.001% to about 2% by weight of the anti-infective composition. When the anti-infective agent is benzalkonium chloride or other aromatic quaternary ammonium halide compound, the concentration within a topical composition is preferably in a range from about 0.01% and to about 0.5% by weight, more preferably in a range from about 0.05% to about 0.3% by weight, and most preferably in a range from about 0.1% to about 0.2% by weight. To avoid toxicity, the concentration can be less than 0.26% by weight and is more preferably about 0.13% by weight.

An important issue when applying the treatment composition to a painful cold sore, shingles, or other disordered tissue is proper compliance by the user. Solvent carriers, such as isopropyl alcohol, ethanol, methanol, acetone, and the like, can cause excruciating pain when applied to sensitive disordered tissues such as cold sores and shingles. Such pain can discourage compliance by the user and undermine the effectiveness of an otherwise effective treatment composition. The treatment composition may therefore also include benzocaine or other topical anesthetic, which can promote compliance by reducing pain and, in some cases, can even enhance penetration of the composition into the disordered tissue.

Unexpectedly, benzocaine or other topical anesthetics, when included in specific amounts, can increase the ability of such treatment compositions to penetrate into the disordered tissue in order for the active agent to more quickly contact and deactivate viruses or other pathogens within the disordered tissue. Benzocaine or other topical anesthetics can also increase patient compliance by reducing the pain associated with application of the anti-infective composition to painful disordered tissue, particularly with open sores. However, beyond merely reducing pain, benzocaine or other topical anesthetics have been found to increase efficacy of treatment because they promotes faster penetration of the treatment composition into disordered tissue, which reduces the amount of rubbing or agitation that would otherwise be required for the composition to be effective.

The amount of benzocaine or other topical anesthetic within the treatment composition is high enough to enhance penetration, and preferably help alleviate pain. However, the amount of benzocaine or other topical anesthetic is advantageously not so high as to leave a residue on the surface of the skin and/or cause loss of sensation in surrounding tissue and/or for a prolonged period of time (e.g., greater than about 15 minutes). For example, if included in excessive amounts, benzocaine or other topical anesthetic can cause numbing of a substantial portion of a person's lips for an extended period of time, which can inhibit normal activities such as drinking and talking (e.g., as can occur after a person leaves a dental office after receiving an injection of novocaine).

The amount of benzocaine or other topical anesthetic is most effective when numbing is temporary and goes away once the treatment composition has effectively penetrated into the disordered tissue and resided long enough in the disordered tissue to deactivate the pathogens and neutralize inflammatory agents in the tissue causing the pain. According to one embodiment, the amount of benzocaine or other topical anesthetic is selected to provide a numbing effect for a time period of about 1 minute to about 20 minutes, preferably about 2 minutes to about 15 minutes, more preferable about 3 minutes to about 10 minutes, and most preferably about 4 minutes to about 8 minutes after numbing first occurs. It is desirable to include an amount of benzocaine or other topical anesthetic so that numbing begins in about 10 seconds or less after application of the treatment composition, preferably in about 8 seconds or less, more preferably in about 6 seconds or less, and most preferably in about 4 seconds or less.

The highly penetrating compositions are formulated so as to penetrate quickly so that the treatment composition is no longer detected on the skin surface after less than about 1 minute, preferably less than about 40 seconds, more preferably less than about 20 seconds, and most preferably less than about 10 seconds. Viruses are deactivated and inflammatory agents are neutralized within minutes or seconds after effective penetration such that it is desirable for the numbing effect of benzocaine or other topical anesthetic to subside in less than about 10 minutes after application, preferably less than about 8 minutes, more preferably less than about 6 minutes, and most preferably less than about 5 minutes.

After extensive comparative survey testing, it was determined that the most effective amount of benzocaine within treatment compositions that also included a liquid carrier comprised of 70% by volume isopropyl alcohol in water and 0.13% by weight benzalkonium chloride was between about 2.5% and about 7.5% by weight. Above 7.5%, a benzocaine residue was sometimes detected. Below about 2%, benzocaine did not significantly enhance penetration. Between about 2.5% to about 7.5%, however, benzocaine enhanced penetration and caused temporary, but not excessive, numbing when using the treatment compositions that were tested. A more optimal range for this anti-infective composition is about 2.75% to about 6% benzocaine by weight, and the most optimal range was found to be about 3% to about 5% benzocaine by weight.

Although less preferred and not as effective as benzocaine in enhancing penetration of penetrating treatment compositions and/or reducing pain without causing undue numbing of a user's lip, other topical anesthetics may be useful in enhancing patient compliance by reducing pain associated with applying penetrating treatment compositions to disordered tissue. Examples of other topical anesthetics that may be used in addition to or instead of include butamben, dibucaine, lidocaine, oxybuprocaine, pramoxine, proparacaine, proxymetacaine, prilocalne, tetracaine, novocaine, bupivocaine, carbocaine, ropivocaine, xylocalne, cocaine, and mixtures thereof. Of the foregoing, butamben may perform most similar to benzocaine given the similarity in the two chemical structures. Other anesthetics include caffeine, nicotine, oil of clove, tea tree oil (melaleuca alternifolia, which also acts as a disinfectant), tronothane, dyclonine, dyclonine hydrochloride, pramoxine hydrochloride, diperodon, butamben picrate, cyclomethycaine sulfate, cyclomethycaine hydrochloride, dimethisoquin hydrochloride, and phenol.

Such other topical anesthetics can be included in amounts similar to those of benzocaine. Alternatively, they can be included in an amount between 2.1% and about 15% by weight of the treatment composition, or between about 2.2% and about 10% by weight, or between about 2.3% to about 8% by weight, or between about 2.5% to about 6% by weight. Such other topical anesthetic, either alone or if combined with another topical anesthetic, such as benzocaine, may be included in an amount so as to numb the treatment area for a time period of about 1 minute to about 20 minutes, preferably about 2 minutes to about 15 minutes, more preferably about 3 minutes to about 10 minutes, and most preferably about 4 minutes to about 8 minutes after numbing first occurs. It is desirable to include an amount of topical anesthetic so that numbing begins in about 10 seconds or less after application of the treatment composition, preferably in about 8 seconds or less, more preferable in about 6 seconds or less, and most preferably in about 4 seconds or less.

The carrier may also include other components that, by themselves, may be too viscous to act as tissue penetrating agents, but which, in combination with water, isopropyl alcohol, and other solvents identified herein or known to those of skill in the art, can penetrate tissue. Such components include ethoxylated alcohols (e.g., lauryl alcohol ethoxylates), ethoxylated nonylphenols (e.g., Nonoxynol-9), low molecular weight glycols (e.g., ranging from ethylene glycol to PEG-400, propylene glycol, propanediol, and the like), ethoxylated amines, and their quaternaries. Certain essential oils and emollients, which are normally water insoluble, can be made soluble in water by ethoxylation (e.g., ethoxylated lanolin).

Penetration inhibiting components include chemicals which are petrolatum based substances, materials conventionally utilized as thickeners, naturally occurring oils, substances derived from naturally occurring oils, or any other substance which is added primarily to increase the tendency of a treatment composition to remain on the surface of disordered tissue such as a cold sore. The term "substantially oil-free" means that oil substances are may be present in an amount of less than about 2% by volume, preferably less than about 1%, more preferably less than about 0.05%, and most preferably less than about 0.01%.

Treatment compositions may include other components that achieve a particular result and do not substantially reduce the ability of the treatment composition to penetrate into the disordered tissue or the ability of the treatment composition to be anti-infective. Examples of such components include pH adjusters, substances having anesthetic qualities, vasodilators, analgesics and defoamers. Example pH adjustors may include organic acids, mineral acids in minute amounts, organic bases or mineral bases also in minute amounts. Example organic acids include citric acid, ascorbic acid, sorbic acid, malic acid, ascetic acid, succinic acid, caproic acid, and the like. Other acids include hydrochloric acid, nitric acid, hydroiodic acid, and the like in minute amounts. Example bases include methyl and ethylamines such as triethanolamine, and the like. Other bases include, ammonium hydroxide, potassium hydroxide, sodium hydroxide, and the like.

Preservatives may be added to the anti-infective composition, including parabens, preferably methyl and propyl parabens. Preservatives, if present, are included in the composition in a range from about 0.0001% to about 0.01% by volume of the treatment composition.

The active agent can also include a nucleoside analogue, nucleoside analogue precursor, nucleotide analogue, or any other anti-viral drug discussed above relative to systemic treatment. Because nucleoside analogues are discussed above in great detail with regard to systemic treatments, they will not be discussed again except to note that the nucleoside analogue should generally be delivered in an active form if used in a topical composition. The active agent may thus be any of the above-cited nucleoside analogues, derivative, or metabolite thereof in order to provide an active form of the active agent. In one embodiment, the same anti-virus drug used in the systemic composition can also be used in a topical composition. Alternatively, a different anti-virus drug can be used.

Topical formulations incorporating an anti-virus drug as active agent, including analogs, metabolites, or derivatives thereof, can include the active agent in an amount of, for example, about 0.01% to about 50% w/w; preferably from about 0.1% to 25% w/w; most preferably from about 1% to about 15% w/w. Other topical formulations incorporating an anti-virus drug may include the active agent in an amount of, for example, from about 0.075% to about 20% w/w, preferably from about 0.2% to about 15% w/w and most preferably from about 0.5% to about 10% w/w.

The active agent could also be another compound that acts to reduce or inhibit viral replication other than by substituting as a nucleotide. In one embodiment, a non-nucleoside includes docosanol or behenyl alcohol (sold under the trademark Abreva™). Docosanol is a 22 carbon straight chain-saturated alcohol. N-docosanol is claimed to inhibit fusion between the plasma membrane and the viral envelope. This prevents viral entry into the cell and, as a result, reduces or disrupts viral replication. When present in a topical formulation, docosonal can be present in a volume range from about 5% to about 15%.

In one embodiment, a nucleoside (e.g., aciclovir) can be formulated as an oil-in-water topical formulation in which the oil is dispersed in an aqueous phase and most of the nucleoside is located in the aqueous phase which, in one embodiment, can comprise water and polyhydric alcohol. A polyhydric alcohol is an alcohol having two or more hydroxyl groups. Polyhydric alcohols suitable for incorporation into topical formulations include glycols and macrogols such as propylene glycol, butane 1,3-diol, polyethylene glycol, glycerol, mannitol, sorbitol, and mixtures thereof. The oil phase or emulsifying wax of the oil-in-water formulation can include a hydrophilic emulsifier (otherwise known as an emulgent) and desirably at least one lipophilic emulsifier such as fat or oil or both to act as a stabilizer. Further details describing how to formulate an oil-in-water topical formulation are contained in U.S. Pat. No. 4,963,555, hereby incorporated by reference.

Other components for the topical compositions include vasodilators such as nitroglycerine and the like. Vasodilators are useful for causing penetration of the active agent or agents into the disordered tissue to its base in the skin or mucous membranes and beyond. Care must be taken to balance the effect of localized vasodilation against the systemic toxicity of the topical composition such that penetration into the disordered tissue is clinically significant, but that the active agent or agents remain substantially local to the disordered tissue for maximum efficacy. Where a vasodilator is supplied to make up the topical composition, it may be provided in a preferred range from about 0.001% to about 0.05% by volume of the topical composition.

Other components for the topical composition include analgesics such as methyl salicylate, aspirin, and other salicylate salts. Other components for their analgesic effects include N,N-dimethyl aspartic acid; N—N-dimethyl glutamic acid, trolamine salicylate, antipyrine, and salicylamide. Where an analgesic is present, it may be supplied to make up the composition in a preferred range from about 0.001% to about 0.01% by volume of the topical composition.

For infections of the eye or other external tissues, e.g., mouth and skin, the formulations are preferably applied as a topical solution, ointment or cream containing the active agent in an effective amount of, for example, 0.075 to 20% w/w, preferably 0.2 to 15% w/w and most preferably 0.5 to 10% w/w. When formulated in an ointment, the active agents may be employed with either paraffinic or a water-miscible ointment base. Alternatively, the active agents may be formulated in a cream with an oil-in-water cream base. In addition topical applications may be made transdermally by means of an iontophoretic device.

Formulations suitable for topical administration to the eye also include eye drops wherein the active agent is dissolved or suspended in a suitable carrier, especially an aqueous solvent for the active agent. The active agent is preferably present in such formulations in a concentration of about 0.5% to about 20%, advantageously about 0.5% to about 10%, and even more preferred about 1.5% w/w.

Formulations suitable for topical administration in the mouth include lozenges comprising the active agent in a flavored basis, usually sucrose and acacia or tragacanth; pastilles comprising the active agent in an inert basis such as gelatin and glycerine, or sucrose and acacia; and mouthwashes comprising the active agent in a suitable liquid carrier.

Formulations suitable for nasal administration wherein the carrier is a solid include a coarse powder having a particle size for example in the range 20 to 500 microns which is administered by rapid inhalation through the nasal passage from a container of powder held close up to the nose. Suitable formulations wherein the carrier is a liquid, for administration as for example a nasal spray or as nasal drops, include aqueous or oily solutions of the active agent.

Formulations suitable for vaginal administration may be presented as pessaries, tampons, creams, gels, pastes, vaginal suppositories, foams or spray formulations containing in addition to the active agent such carriers as are known in the art to be appropriate. Formulations for rectal administration may be presented as a suppository with a suitable base comprising for example cocoa butter or a salicylate or may be a paste or cream applied into the anus via an applicator ("pile pipe").

The topical compositions can be applied to various parts of a person's body in a variety of ways. In one embodiment, the topical composition is applied using a person's hand or finger. In another embodiment, an applicator is used. An applicator can be beneficial to prevent oils, bacteria, or other contamination from a person's hands to contact the infected site in order to prevent further opportunistic infection of the vulnerable area. If an applicator is used, preferably, the applicator is sterile.

Applicators may form part of a method and system for applying the treatment compositions. As such, applicators may be preconfigured with particular mixtures to treat specific disorders, such as cold sores, chickenpox, herpes zoster (shingles), genital herpes, and the like. Examples of applicators include those taught in U.S. Pat. No. 6,211,243 (Johnson), U.S. Pat. No. 5,709,866 (Booras et al.), U.S. Pat. No. 5,704,906 (Fox), U.S. Pat. No. 5,527,534 (Mythling), U.S. Pat. No. 5,016,651 (Stalcup et al.), U.S. Pat. No. 4,887,994 (Bedford), and U.S. Pat. No. 4,952,204 (Korteweg), the disclosures of which are incorporated herein by reference. Example applicators include prepackaged applicators with agitation pads impregnated with the treatment composition. An applicator may be provided as a unitary structure such as a sealed container that is frangible and configured for a single use.

A method of topically administering the anti-infective composition includes impregnating an applicator with the topical composition and contacting the treatment site with the applicator. Agitation and/or compression of the disordered tissue may be useful to enhance penetration of the composition. It may also stimulate the immune system by causing trauma to the disordered tissue.

IV. Combination of Systemic and Topical Treatments

Combining systemic treatment of disordered tissue caused by a virus using a pharmaceutically acceptable quantity of anti-virus drug with topical administration of an anti-infective composition to the disordered tissues results in greater efficacy of treatment. Even though topical administration of an anti-infective composition is not recognized by the FDA or scientific community as being therapeutically effective to systemically eradicate viruses that cause disordered tissues, it has now been found that topically administering an anti-infective composition to disordered tissue while systemically administering an anti-virus drug unexpectedly results in greater systemic treatment of the virus. In other words, a topical treatment that is itself non-systemic in nature unexpectedly exhibits a systemic treatment effect when used in combination with a systemically administered anti-virus drug. The systemic treatment effect is exhibited by a reduction in the amount of time and/or number of dosages required by the systemically administered anti-virus drug to otherwise systemically treat the disease by itself, in the absence of topical treatment with an anti-infective composition.

One explanation for this phenomenon, postulated by the inventor, is that viruses that cause disordered tissues to erupt on mammalian skin become locally concentrated at the disordered tissue site. This makes such viruses more difficult to treat using systemically administered anti-virus drugs, which may not easily penetrate through the stratum basal layer to the epidermis. Instead, such viruses are more easily deactivated using a topically administered anti-infective composition that can penetrate through the outer layer of skin and attack the viruses at the disordered tissue site. It is postulated that deactivation of such viruses at the disordered tissue site using a penetrating anti-infective topical composition reduces the overall number of viruses in the patient's body that must be treated by the systemic drug, thereby significantly reducing the amount of time and/or dosages of systemic drug that would otherwise be required to treat the outbreak using the systemic drug by itself. In addition, it is postulated that, to the extent the stratum basal layer inhibits systemic medication from passing through to the epidermis, topically treating and deactivating viruses at the disordered tissue site may be more effective than deactivating such viruses using the systemic treatment. The result is synergistic dual treatment of the disease by the systemic drug, which is effective in treating viruses internally but less effective at the skin surface, coupled with topical treatment of the disordered tissue using a penetrating anti-infective composition, which is effective in deactivation of viruses near the skin surface but not internally beyond the disordered tissue site.

Co-administration of a systemic anti-viral drug and a topically administered penetrating anti-infective composition has also been found to reduce or eliminate post-herpetic neuralgia, which is caused by nerve damage. This is unexpected since systemic anti-viral drugs on their own can often resolve the acute symptoms associated with disordered tissues yet not prevent nerve damage and/or chronic neuralgia, which is an extremely painful neurological condition for which there is no known cure.

Post-Herpetic Neuralgia (PHN) is a complication arising in some cases of herpes zoster (shingles). It can involve very sharp pains long after visible signs and symptoms of shingles have abated. It can last days, weeks, months, years, or decades. The risk of PHN is the principal reason that some physicians prescribe anti-depressants. PHN has been a factor in elderly suicide. It is important to understand that not everyone who gets singles also gets post-herpetic neuralgia. However, there are several factors that influence PHN. The older the patient, the greater the chance of PHN. The longer one has visible signs and symptoms, the greater the risk of PHN. And, whether or not the patient was previously vaccinated will affect the chances, duration, and severity of PHN. Likewise, timely dosing with nucleoside analogue drugs (within the first 72 hours of first signs and symptoms) can reduce the risk of and/or the severity of PHN, but it will not eliminate the risk of PHN. Thus, combining systemic and topical treatments of disordered tissues caused by viruses, such as the herpes zoster virus, has a synergistic effect that is not expected and which is not demonstrated why either treatment is performed separately.

Example methods of dual treatment include systemically administering one or more dosages of a pharmaceutically acceptable amount of one or more anti-virus drugs as disclosed herein. The amount and timing of systemic administration of one or more anti-virus drugs can be the same as those followed according to standard treatment protocols. For example, when using anti-virus drugs such as acyclovir, penciclovir (sold under the trademark Denavir®), famciclovir (sold under the trademark Famvir®), idoxuridine, ganciclovir (sold under the trademark Cytovene®), cidofovir (sold under the trademark Vistide®), and/or valaciclovir, the dosages and timing of administrating can be substantially identical or similar to those recommended by the manufacturer and/or as typically prescribed by doctors. An important difference, however, is that the overall treatment time and/or number of dosages when using such anti-virus drugs can be reduced when such drugs are co-administered together with topical administration of one or more anti-infective compositions as disclosed herein to the disordered tissue site.

Administration of the anti-infective composition can be as is disclosed herein and/or as described in any of U.S. Pat. Nos. 6,211,243, 6,410,599, 6,414,032, 6423,750, 6,759,434, 8,173,709, and 8,217,080 (all to Johnson), herein incorporated by reference. In its simplest form, the anti-infective composition is applied using an appropriate applicator device and/or using the person's or healthcare professional's hand or finger in order to cause or allow the anti-infective composition to penetrate sufficiently into the disordered tissue in order to kill viruses at the disordered tissue site.

FIG. 1 depicts a vertical cross-section of the epidermis and the papillae of the dermis. The stratum corneum 28 is disposed upon the fatty layer or stratum lucidum 30. The stratum lucidum is disposed over the stratum granulosum 32. Below the stratum granulosum 32 is the stratum spinosum 34. Typically, the stratum spinosum 34 has a lipid film disposed around each individual cell. Below the stratum spinosum 34 is the stratum basale 38 that overlies vascularized tissue. Within the vascularized tissue the nervous papilla of the corium 36 is located along with blood vessels and nerves 40. It is postulated that, during a viral outbreak that causes painful disordered to tissue to form on a person's skin, a disproportionate number of disease-causing viruses are concentrated at or near the nervous papilla of the corium 36, surrounding vascularized tissue, and stratum spinosum 34. Because of this, systemic treatment using system anti-virus drugs may be less effective in treating viruses at the disordered tissue site, since the drug may have difficulty penetrating the stratum basal layer 38.

During application of the topical anti-infective composition, an applicator 12 saturated with penetrating anti-infective composition 22 can be used. To further enhance penetration of anti-infective composition 22 into the various layers of tissue in order to reach the viruses, the applicator 12 can be vigorously agitated across the stratum corneum 28 in order to cause or allow anti-infective composition 22 to penetrate therethrough. The arrows illustrate exemplary agitation movement. Application of pressure may be as effective, or even more effective, than agitation in order to cause or allow penetration of anti-infective composition 22 through the various layers and to the viruses. It is postulated that anti-infective composition 22 may move through the stratum corneum 28 without significant rupture thereof due to the vigorous agitation thereon. Application of pressure may further increase the ability of composition 22 to penetrate as pressure may flatten or compress the layers and assist in forcing composition 22 downward through the layers. Anti-infective composition 22 can penetrate to the nervous papilla of the corium 36 by the combination of vigorous agitation, pressure and/or the penetrating nature of the composition. Composition 22 may reside in reservoir amounts within the stratum spinosum 34 and may diffuse over time across the stratum basale 38 to the nerve endings.

The length of time that the anti-infective composition is applied to the disordered tissue, such as by vigorous agitation and/or pressure, may vary according to the individual, the size of the applicator surface in relation to the size of the disordered tissue being treated, the amount of pressure applied and oscillation rate of rubbing. Typically, application of the composition can be maintained for at least 1 second and is more typically maintained for a period of time in a range from about 3 seconds to about 1 minute, or about 5 seconds to about 15 seconds.

Dual systemic and topical treatment of disordered tissue means that the systemic anti-virus drug and topically administered anti-infective composition are applied in roughly the same time frame. For example, the systemic and topical treatments can be administered within 1 hour of each other (e.g., simultaneously, or within 30 minutes, 15 minutes, 10 minutes, 5 minutes, or 1 minute of each other). In another embodiment, the systemic and topical treatments can be administered within 12 hours of each other. In another embodiment, the systemic and topical treatments can be administered within 24 hours of each other. In still another embodiment, the systemic and topical treatments can be administered within 2 days of each other.

Such combined use of systemic and topical compositions provides synergistic results in eliminating an infectious virus. First, it is postulated that the systemic and topical compositions act simultaneously on both sides of the stratum basale layer 38 (FIG. 1) of the epidermis to eliminate the infectious virus. While employing only one of either systemic or topical treatment, as is typical in the art of treating cold sores, shingles or other disordered tissue, the infectious virus is left to multiply on at least one side of the stratum basale layer of the epidermis. This results in less effective elimination of the infectious virus. It also makes reinfection more likely.

V. EXAMPLES

Following are examples of compositions and kits that can be used to carry out the inventive methods as well as comparative examples of treatments using only systemic anti-viral drugs to treat herpes related disordered tissues.

Comparative Examples 1-3

The following are examples of known regimens for treating Herpes Zoster (shingles) using systemic anti-viral drugs (source: http://www,aafp.org./afp/2000/0415/p2437.html, Stankus, et al., Management of Herpes Zoster (Shingles) and Postherpetic Neuralgia, *Am Fam Physician.* 2000 Apr. 15; 61(8):2437-2444).

| Comparative Example | Drug | Dosage | Average Cost* (in 2000) |
|---|---|---|---|
| 1 | Acyclovir (Zovirax)† | 800 mg orally five times daily for 7 to 10 days; 10 mg per kg IV every 8 hours for 7 to 10 days‡ | $174 to 248 |
| 2 | Famciclovir (Famvir)† | 500 mg orally three times daily for 7 days | $140 |
| 3 | Valacyclovir (Valtrex)† | 1,000 mg orally three times daily for 7 days | $84 |

IV = intravenously.
*Estimated cost to the pharmacist based on average wholesale prices (rounded to the nearest dollar), for seven days of therapy, in Red book. Montvale, N.J.: Medical Economics Data, 2000. Cost to the patient will be higher, depending on prescription filling fee.
†Antiviral therapy has been shown to be beneficial only when patients are treated within 72 hours of onset of the herpes zoster rash. Antiviral agents are not used in combination, and selection of an agent is based on dosage schedule and cost.
‡Acyclovir can be administered IV to severely immunocompromised patients or patients who are unable to take medications orally.

When using any one of the foregoing systemic anti-viral drugs used to treat shingles and other viral tissue disorders, one of ordinary skill in the art would assume that they work as expected to slow or inhibit replication of the virus within the patient's body even if the outward symptom of painful lesions and disordered tissue do not immediately resolve. The fact that doctors continue to prescribe the medications in these example and similar anti-viral medications for treatment of various herpetic tissue disorder outbreaks means they are considered to be the standard of care and are safe and effective in treating such disorders.

In the following examples, both systemic and topical treatments were used to treat disordered tissue outbreaks. The topically administered anti-infective compositions were demonstrably able to provide immediate relief from the outward symptoms of the disordered tissue, both in terms of relieving pain caused by disordered tissue lesions and also causing faster healing of the disordered tissue lesions. Nevertheless, because the use of systemic anti-viral drugs continues to be the standard of care for treating such ailments, one of ordinary skill in the art would expect that administering the systemic anti-viral drug would be effective in treating the long-term effects of the disordered tissue outbreak. The fact that co-administration of a topical anti-infective composition not only provided faster outward relief of the symptoms of disordered tissue but also shortened the duration of overall healing and reduced both short-term pain and post-herpetic neuralgia more effectively than administering a systemic anti-viral drug by itself was surprising and unexpected. This demonstrates the synergistic benefits obtained by combining systemic and topical treatments of viral disordered tissues, such as herpes zoster (shingles) and other herpetic diseases.

Example 4

A female, age 45, with a clinical history of recurrent Herpes Zoster (HZV) (or in layman's terms, shingles) experienced a recurrent outbreak after a stressful week at work and a weekend in the sun following a trip to a tanning booth. (It is known that stress and UV-B can both trigger herpetic outbreaks.) This subject had her first episode with HZV about one year prior. She was diagnosed by her physician and given a prescription for Zovirax (acyclovir). She took the Zovirax, but experienced lesions lasting 3-4 weeks and experienced over 12 weeks of post herpetic neuralgia. The previous episode included all the classic stages, including weeping, but only involved several very small lesions.

The subject then became aware of preliminary studies combining the use of systemic drugs such as acyclovir and a topically administered anti-infective composition within the scope of the disclosure. The topically administered anti-infective composition (Viroxyn® Professional, used to treat cold sores) was an isopropyl alcohol tincture of benzalkonium chloride, 0.13%, and 7.5% benzocaine.

The recurrence of shingles that was treated with a combination of acyclovir and Viroxyn® Professional was in the beginning of the third day and had progressed from prodromal "tingle", through papule (raised bump), to vesicle. By this time some of the vesicles had ulcerated, perhaps as a result of inadvertent scratching of the lesions by the patient despite her best efforts not to scratch them. There was also a "rash like" appearance near the ulcerated lesions that is typical of herpes zoster. At the time of treatment, she reported intense pain and some itching. She reported that the pain was local to the lesion site, but her overall discomfort had made it difficult to sleep the night before. The lesions were located in the chest area and covered approximately ¼ of the upper chest area, spreading up onto the shoulders. They varied in size from the smallest, which was about 3×5 mm, to the largest, which was a series that had joined confluent to form a lesion area of about 18×25 mm. The subject reported that this was the worst episode of HZV she had ever experienced in all aspects. It was the most painful, covered the largest area, and was the most bothersome.

Prior to treatment at 10:00 am, the lesions and rash were consistent with herpes zoster lesions, but epithelial damage was still limited, probably due to the early stage of the disease progression. Due to the extensive area covered by the lesions, approximately 30 vials of single dose Viroxyn® Professional cold sore medication were needed to treat all the lesion sites and rash. In addition to taking acyclovir, the Viroxyn® Professional solution was rubbed onto each sore site in accordance with the recommended directions for treatment of Herpes Labialis (i.e., cold sores). Following treatment, the area was vigorously washed using bulk Viroxyn® Professional solution.

The subject reported a gradual loss of pain, itching, and burning during the day of treatment with Viroxyn® Professional. She had no trouble with sleep that night. The next day, all pain, itching, and burning had subsided and the lesions were beginning to scab. Four (4) days following treatment, all but a few small scabs had fallen off. No other symptoms were present at the time of this report, which was 16 days following treatment. There were no adverse events. This example demonstrates the greatly enhanced and synergistic benefits of combining systemic treatment using an anti-viral drug with topical administration of a penetrating anti-infective composition to disordered tissue caused by herpes zoster.

Example 5

An 83 year old retired physician phoned Quadex (the manufacturer of Viroxyn® Professional) to dictate her own case history. She was living in an assisted living center when she developed signs and symptoms of herpes zoster (shingles). She did not immediately identify these signs and symptoms and instead thought that they were a mild skin irritation. By the time she realized that she did indeed have shingles, the 72-hour window of effective treatment potential with nucleosides was dangerously close to expiring.

She prescribed valacyclovir (Valtrex) for herself and requested a ride to the pharmacy. While waiting, she remembered that her dentist had given her a sample 3-pack of Viroxyn® Professional to treat her occasional bouts with herpes labialis (cold sores). While she did not expect that the anti-viral ingredient would be able to treat her shingles, she wanted to take advantage of the benzocaine for temporary relief of the discomfort.

When she phoned in her case report, she reported that she had been astounded when after less than one hour, and well after the topical anesthetic effect of the benzocaine had worn off, her physical discomfort began to abate and was fully resolved within one-half day. Within 24 hours the rash and papule like symptoms of shingles had begun to fade and she was completely normal in appearance within 48 hours and experienced no post-herpetic neuralgia. Topical treatment of the disordered tissue site with a penetrating anti-infective agent greatly shortened the time to recovery that otherwise would have been required had the patient taken Valtrex by itself.

Example 6

A 62 year old female was vacationing in California when she developed a red rash and subsequent lesions on her right buttock. She was diagnosed with herpes zoster (shingles) on day 2 after first signs and symptoms were noted and was prescribed valacyclovir (Valtrex) per label. However, the Valtrex showed little noticeable effect initially.

On day 18 after first signs and symptoms, and after having completed a Valtrex regimen as prescribed by a physician, she still had open herpetic lesions and was in so much pain that she found it difficult to sleep and impossible to sit. As flying was the only way to get to her home from California, she and her husband elected to extend their time in California.

On day 18, her husband was so desperate that he phoned a healthcare provider that he knew who also had experience treating cold sores with Viroxyn® Professional. The husband asked if anything could be done and the healthcare provider phoned Quadex for a consultation with Dr. McCarthy. A large sample of Viroxyn® Professional was sent by overnight delivery to California with instructions for use. The husband later confessed that he did not follow the directions for treating cold sores due to the intensity of his wife's pain. Instead of rubbing (as is prescribed when treating cold sores) he merely dabbed it on. However, after 1 hour the wife was feeling better and self-applied the medication according to directions, including rubbing the composition into the disordered tissue lesions. Her pain began to abate 10 to 20 minutes after application and she fell asleep with no difficulty. She awoke one day after treatment with Viroxyn® Professional and was startled that her pain was completely gone and the lesions were in soft scab. She went on to complete healing within a week with no post-herpetic neuralgia.

This case history is extremely significant in that persons who experience longer bouts with active lesions are at significantly greater risk of post-herpetic neuralgia than those who resolve more quickly. However, the combined use of Valtrex systemically and topically administering a penetrating anti-infective composition to the disordered tissue site eliminated both the immediate symptoms of shingles as well as long-term post-herpetic neuralgia.

Example 7

A 72 year old male who had knowledge of Viroxyn® Professional for use on cold sores began to experience a rash and pain on his lower back. He saw a physician and was prescribed Valtrex. He had been on Valtrex for a day or so when he presented for treatment with Viroxyn® Professional.

The area of shingles presentation began at the spine and began to travel along his right side toward the front of his body. The area was reddish with an element of purple and papule like bumps were beginning to form. He was treated with Viroxyn® Professional using vigorous rubbing and told to present again the next day. He did so and the treated area was no longer red and inflamed, but rather light pink. He reported loss of pain in the treated area, but had a new area of presentation extending yet another 6 inches. This area was red and inflamed. The new presentation was treated with Viroxyn® Professional and the man told to come back again the next day.

On day 3 of treatment, the first area that was treated was back to normal condition. The area treated the day before was no longer red and inflamed and was a light pink color, but a third area of shingles was progressing forward from the first two treated areas. This too was treated with Viroxyn® Professional.

The man was again examined 2 days after the treatment ended and was completely free of visual signs and symptoms and reported persistent loss of discomfort with no post-herpetic pain. This case study again demonstrated the synergistic effect and unexpected benefit obtained by combining systemic treatment using an anti-viral drug with topical treatment of the disordered tissue using a penetrating anti-infective composition.

Example 8

A Caucasian female, age 37, used Viroxyn® Professional in conjunction with Valtrex to treat Shingles in 2012. The shingles infection started out by what was assumed to be a small cut or lesion. It started itching and burning. The patient thought that it was just a cut or other wound. Then the lesion grew and started to spread. Then the patient noticed three on her leg, then four. Then the patient started getting little bumps all over her legs. It started to spread up her leg, to her thigh, and then to her lower trunk. They started out itching and opening up and then they bled and leaked infection.

The patient initially went to the doctor in the early stages of the infection when it was only on her leg. The doctor diagnosed the condition as shingles and prescribed the patient Valtrex. Shortly after taking the first doses the lesions spread up the patient's leg and to her lower trunk. The bumps were smaller but they kept spreading. The doctor advised her to keep taking the Valtrex. Once the patient finished the first prescription of Valtrex, the doctor provided a second Valtrex prescription. At this time, the sores on the patient's leg were still open and large. The sores remained the same size although the sores on the patient's leg were much larger than on her lower trunk.

Just after the patient started the second prescription of Valtrex she began applying Viroxyn® Professional everywhere and the sores began to resolve in around two days. She had three lesions that were severe and open on her leg. She started treating them with Viroxyn® Professional, which application was initially painful but the lesions started closing. All of the lesions treated with Viroxyn® Professional went away and do not hurt anymore, but the area of the three large ones that were open still hurt even though the lesions themselves are all healed and about five months has passed. These areas still burn and cause the patient pain, which is consistent with post-herpetic neuralgia. Nevertheless, the patient was astonished at how fast the lesions closed up once she began administering both Valtrex systemically and Viroxyn® Professional topically to the disordered tissue sites.

This example shows that early treatment of disordered tissue combining the use of a systemic anti-virus drug and topical administration of a penetrating anti-infective composition to the disordered tissue site before the lesions burst and become open sores is more effective in preventing post-herpetic neuralgia. The fact that the patient was able to prevent post-herpetic neuralgia on most lesions demonstrates the synergistic benefit of combined systemic and topical treatment of disordered tissue caused by a virus. Had the patient used only the systemic anti-virus drug, she would likely have had more widespread post-herpetic neuralgia in the area of all the lesions had they all burst and become open sores like the ones that still cause lingering pain.

Example 9

A 40 year old male had shingles on his neck and shoulders. H is brother is a physician and diagnosed shingles and prescribed a nucleoside drug according to FDA approved labeling. The lesions had started to propagate down the affected dermatomes of the shoulder and neck. The lesions continued to progress despite anti-viral therapy.

A family member recommended that the patient try Viroxyn® Professional. Even though systemic nucleoside analogue therapy is "Standard of Care" and the patient received a timely prescription, the lesions did not resolve in a timely manner with standard of care. Indeed, the disease appeared to progress unabated. Surprisingly, the co-therapy of systemic nucleoside and topical anti-microbial worked together to begin to resolve both the lesions and the physical discomfort (pain, itching, and burning). The physical discomfort symptoms from the lesions was abated in about 1 hour. Erythema resolved and lesions healed within 2 days. This outcome would not be anticipated and surprised the physician who diagnosed and treated the shingles in this example.

Example 10

Another adult male contracted shingles and developed lesions on the face and in the white of his eye. In addition to taking an anti-viral drug, a penetrating anti-infective composition similar to Viroxyn® Professional was used to treat all lesions, including the one in the patient's eye. Even though placing chemicals in the eye can be irritating, when used properly they may have no long term damaging effect, unlike shingles, which can cause blindness. As a result of the combined treatment, all lesions cleared up and the patient has good vision in the previously infected eye. This demonstratesd the synergistic effect and unexpected benefit obtained by combining systemic treatment using an anti-viral drug with topical treatment of the disordered tissue using a penetrating anti-infective composition.

Example 11

Dual systemic and topical treatment of disordered tissues caused by a virus involve the use of Viroxyn® Professional and at least one of the following anti-viral drugs:

aciclovir (acycloguanosine) (2-Amino-1,9-dihydro-9-((2-hydroxyethoxy)methyl)-6H-purin-6-one), penciclovir (2-amino-9-[4-hydroxy-3-(hydroxymethyl)butyl]-6,9-dihydro-3H-purin-6-one) (sold under the trademark Denavir®), famciclovir (2-[acetyloxy)methyl]-4-(2-amino-9H-purin-9-yl)butyl acetate) (sold under the trademark Famvir®), idoxuridine (1-[(2R,4S,5R)-4-hydroxy-5-(hydroxymethyl) oxolan-2-yl]-5-iodo-1,2,3,4-tetrahydropyrimidine-2,4-dione), ganciclovir (2-amino-9-{[(1,3-dihydroxypropan-2-yl)oxy] methyl}-6,9-dihydro-3H-purin-6-one) (sold under the trademark Cytovene®), cidofovir (({[(S)-1-(4-amino-2-oxo-1,2-dihydropyrimidin-1-yl)-3-hydroxypropan-2-yl]oxy}methyl)phosphonic acid) (sold under the trademark Vistide®), and derivatives thereof, or valaciclovir (S)-2-[(2-amino-6-oxo-6,9-dihydro-3H-purin-9-yl)methoxy]ethyl-2amino-3-methylbutanoate) (sold under the trademark Valtrex®).

The one or more systemic anti-viral drugs are administered according to known protocols. The Viroxyn® Professional is applied to the disordered tissue in 1-3 applications and in an amount to saturate or bath the disordered tissue with anti-infective composition. The dual treatment is far more effective in treating the systems and long-term effects of disordered tissues caused by a virus.

Example 12

Dual systemic and topical treatment of disordered tissues caused by a virus involve the use of any of the following drugs of Example 11 in combination with one or more anti-infective compositions that include 70% isopropyl alcohol as the carrier, 0.13% benzalkonium chloride, and one of the following amounts of benzocaine: 0%, 2%, 2.5%, 3%, 4%, 5%, 6%, 7%, 8%, 9%, 10%, 11%, 12%, 13%, 14% or 15%.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of treating disordered tissue caused by a virus in a mammal, comprising:
administering an effective amount of a systemic anti-virus drug to a mammal in need thereof in order to disrupt or inhibit virus replication systemically within the mammal, wherein the systemic anti-virus drug is selected from the group consisting of acyclovir, valaciclovir, penciclovir, famciclovir, ganciclovir, cidofovir, adefovir, tenofovir, and combinations thereof; and topically administering an anti-infective composition comprising at least one anti-infective agent to the disordered tissue of the mammal in order for the composition to penetrate below the disordered tissue surface and independently kill viruses at the disordered tissue site, wherein the at least one anti-infective agent comprises benzalkonium chloride.

2. A method as in claim 1, wherein the anti-infective composition further comprises a liquid carrier having a tissue penetrating component.

3. A method as in claim 2, wherein the tissue penetrating component comprises a lower alkyl solvent and water.

4. A method as in claim 3, wherein the lower alkyl solvent comprises at least one of isopropyl alcohol, ethyl alcohol, or acetone.

5. A method as in claim 2, wherein the anti-infective composition is free of oils or other compounds that inhibit penetration.

6. A method as in claim 1, wherein the method comprises administering a plurality of dosages of the systemic anti-virus drug periodically over a prescribed period of time.

7. A method as in claim 6, wherein topically administering the anti-infective composition reduces the time and/or number of dosages of the systemic anti-virus drug required to treat the disordered tissue and promote healing of one or more lesions at the disordered tissue site compared to treating the disordered tissue using the anti-virus drug by itself in the absence of topically administering the anti-infective composition to the disordered tissue.

8. A method as in claim 7, wherein topically administering the anti-infective composition reduces the time and/or number of dosages of the systemic anti-virus drug required to treat the disordered tissue and promote healing of one or more lesions at the disordered tissue site by at least about 10% compared to treatment of the disordered tissue and healing of the one or more lesions using the anti-virus drug by itself in the absence of topically administering the anti-infective composition to the disordered tissue.

9. A method as in claim 7, wherein topically administering the anti-infective composition reduces the time and/or number of dosages of the systemic anti-virus drug required to treat the disordered tissue and promote healing of one or more lesions at the disordered tissue site by at least about 20% compared to treatment of the disordered tissue using the anti-virus drug by itself in the absence of topically administering the anti-infective composition to the disordered tissue.

10. A method as in claim 7, wherein topically administering the anti-infective composition reduces the time and/or number of dosages of the systemic anti-virus drug required to treat the disordered tissue and promote healing of one or more lesions at the disordered tissue site by at least about 30% compared to treatment of the disordered tissue using the anti-virus drug by itself in the absence of topically administering the anti-infective composition to the disordered tissue.

11. A method as in claim 7, wherein topically administering the anti-infective composition reduces or eliminates the incidence of post treatment neuralgia compared to when treating the disordered tissue using the anti-virus drug by itself in the absence of topically administering the anti-infective composition to the disordered tissue.

12. A method as in claim 7, wherein the method comprises topically administering 5 dosages or less of the anti-infective composition throughout the entire treatment process.

13. A method as in claim 7, wherein the method comprises topically administering 3 dosages or less of the anti-infective composition throughout the entire treatment process.

14. A method as in claim 7, wherein the method comprises topically administering a single dosage of the anti-infective composition throughout the entire treatment process.

15. A method as in claim 1, wherein at least one dose of the systemic anti-virus drug and the anti-infective composition are administered substantially simultaneously.

16. A method as in claim 1, wherein at least one dose of the systemic anti-virus drug and the anti-infective composition are administered within 2 hours of each other.

17. A method as in claim 1, wherein at least one dose of the systemic anti-virus drug and the anti-infective composition are administered within 12 hours of each other.

18. A method as in claim 1, wherein at least one dose of the systemic anti-virus drug and the anti-infective composition are administered within 1 day of each other.

19. A method as in claim 1, wherein the anti-infective composition further comprises at least one topical anesthetic.

20. A method as in claim 19, wherein the at least one topical anesthetic is included in an amount so as to enhance efficacy of the anti-infective composition in treating the disordered tissue and accelerate healing of the disordered tissue.

21. A method as in claim 19, wherein the at least one topical anesthetic is selected from the group consisting of benzocaine, butamben, dibucaine, lidocaine, oxybuprocaine, pramoxine, proparacaine, proxymetacaine, novocaine, tetracaine, and combinations thereof.

22. A method of treating disordered tissue caused by a virus in a mammal, comprising:
systemically administering a pharmaceutically effective amount of an anti-virus drug to a mammal in need thereof in order to disrupt or inhibit virus replication systemically within the mammal, wherein the anti-virus drug comprises at least one of acyclovir, valaciclovir, penciclovir, famciclovir, ganciclovir, cidofovir, adefovir, or tenofovir; and
topically administering an anti-infective composition comprising at least one anti-infective agent to a lesion at a disordered tissue site of the mammal in order for the anti-infective composition to penetrate below a surface of the lesion without rapidly diffusing beyond the skin and into the bloodstream and kill or deactivate viruses at the disordered tissue site, wherein the anti-infective composition comprises benzalkonium chloride and a tissue penetrating liquid carrier,
wherein topically administering the anti-infective composition reduces the time and/or number of dosages of the systemic anti-virus drug required to treat the disordered tissue and promote healing of the lesion by at least about 10% compared to treatment of the disordered tissue using the anti-virus drug by itself in the absence of topically administering the anti-infective composition to the disordered tissue.

23. A method as in claim 22, wherein topically administering the anti-infective composition reduces or eliminates the incidence of post treatment neuralgia compared to when treating the disordered tissue using the anti-virus drug by itself in the absence of topically administering the anti-infective composition to the lesion.

* * * * *

UNITED STATES PATENT AND TRADEMARK OFFICE
CERTIFICATE OF CORRECTION

PATENT NO.        : 9,125,911 B2
APPLICATION NO.   : 13/804002
DATED             : September 8, 2015
INVENTOR(S)       : Johnson It is certified that error appears in the above-identified patent and that said Letters Patent is hereby corrected as shown below:

In the specification

Column 5
Line 33, change "[Racetyloxy)methyl]" to --[(acetyloxy)methyl]--

Column 10
Line 46, change "typically be administered" to --typically administered--

Column 11
Line 8, change "one or ordinary" to --one of ordinary--

Column 17
Line 52, change "substance are may be" to --substances may be--

Column 21
Line 22, change "singles" to --shingles--

Column 22
Line 9, change "disordered to tissue" to --disordered tissue--

Column 27
Line 38, change "H is brother" to --His brother--

Column 28
Line 2, change "demonstratesd" to --demonstrated--

Signed and Sealed this
Eighth Day of March, 2016

Michelle K. Lee
*Director of the United States Patent and Trademark Office*